(12) United States Patent
Chvatal et al.

(10) Patent No.: US 9,983,198 B2
(45) Date of Patent: May 29, 2018

(54) SYSTEMS AND METHODS FOR ASSESSING DATA COLLECTED FROM AN ELECTRICALLY ACTIVE CELL CULTURE

(71) Applicant: Axion BioSystems, Inc., Atlanta, GA (US)

(72) Inventors: Stacie Ann Chvatal, Lawrenceville, GA (US); Daniel Christopher Millard, Atlanta, GA (US); James David Ross, Decatur, GA (US)

(73) Assignee: Axion BioSystems, Inc., Atlanta, GA (US)

( * ) Notice: Subject to any disclaimer, the term of this patent is extended or adjusted under 35 U.S.C. 154(b) by 0 days. days.

(21) Appl. No.: 15/076,223

(22) Filed: Mar. 21, 2016

(65) Prior Publication Data

US 2016/0274088 A1    Sep. 22, 2016

Related U.S. Application Data

(60) Provisional application No. 62/135,382, filed on Mar. 19, 2015.

(51) Int. Cl.
*G01N 33/50* (2006.01)
*H04L 29/08* (2006.01)
(Continued)

(52) U.S. Cl.
CPC ..... *G01N 33/5044* (2013.01); *G01N 33/5091* (2013.01); *H04L 67/12* (2013.01);
(Continued)

(58) Field of Classification Search
CPC ..... A61B 5/04; A61B 5/0464; G01N 33/5044
See application file for complete search history.

(56) References Cited

U.S. PATENT DOCUMENTS 8,560,054 B2    10/2013  Badilini
2004/0106095 A1*  6/2004  Thomson ........... G01N 33/5008
                                                                435/4
(Continued)

OTHER PUBLICATIONS

Caspi, O., et al., "In Vitro Electrophysiological Drug Testing Using Human Embryonic Stem Cell Derived Cardiomyocytes," Stem Cells and Development, vol. 18, No. 1, 2009, pp. 161-172.
(Continued)

*Primary Examiner* — Jonathan M Hurst
(74) *Attorney, Agent, or Firm* — Meunier Carlin & Curfman LLC

(57) ABSTRACT

Disclosed herein are systems and methods for assessing electrically active cell cultures. Optionally, the data can be collected using a microelectrode array (MEA). For example, electrically active cells, such as cardiomyocytes, are cultured such that they are in electrical communication with at least a portion of the electrodes of a well of the MEA. The assessments derived from the disclosed methods may be used to reduce the effects of confounding variables in data obtained from an electrically active cell culture. The methods may also be used to determine a quantitative measure of arrhythmia burden. The methods may also be used to decide if a particular culture or set of data is suitable for inclusion in scientific and characterization studies. Also disclosed is a method of finding the global conduction velocity of an electrically active cell culture.

9 Claims, 31 Drawing Sheets

(51) Int. Cl.
    *A61B 5/04*      (2006.01)
    *A61B 5/0464*    (2006.01)
(52) U.S. Cl.
    CPC ............... *A61B 5/04* (2013.01); *A61B 5/0464* (2013.01); *G01N 33/5058* (2013.01); *G01N 33/5061* (2013.01); *G01N 2800/326* (2013.01)

(56) References Cited

U.S. PATENT DOCUMENTS

| | | | | |
|---|---|---|---|---|
| 2011/0300569 | A1* | 12/2011 | Li | G01N 33/4836 435/29 |
| 2012/0107861 | A1 | 5/2012 | Abrams et al. | |
| 2013/0274838 | A1* | 10/2013 | Entcheva | A61N 5/0601 607/89 |

OTHER PUBLICATIONS

Clements, M., et al., "High-Throughput Multi-Parameter Profiling of Electrophysiological Drug Effects in Human Embryonic Stem Cell Derived Cardiomyocytes Using Multi-Electrode Arrays," Toxicological Sciences, 2014, 17 pages.

Gilchrist, K.H., et al., "High-throughput cardiac safety evaluation and multi-parameter arrhythmia profiling of cardiomyocytes using microelectrode arrays," Toxicology and Applied Pharmacology, http://dx.doi.org/10.1016/j.taap.2015.07.024, 2015, 9 pages.

Guo, L., et al., "Refining the Human iPSC-Cardiomyocyte Arrhythmic Risk Assessment Model," Toxicological Sciences, vol. 136, No. 2, http://www.ncbi.nlm.nih.gov/pubmed/24052561, 2013, pp. 581-594.

Kehat, I., et al., "High-Resolution Electrophysiological Assessment of Human Embryonic Stem Cell-Derived Cardiomyocytes: A Novel In Vitro Model for the Study of Conduction," Circulation Research, Journal of the American Heart Association, vol. 91, 2002, pp. 659-661.

Nakamura, Y., et al., "Assessment of Testing Methods for Drug-Induced Repolarization Delay and Arrhythmias in an iPS Cell-Derived Cardiomyocyte Sheet: Multi-site Validation Study," Journal of Pharmacological Sciences, vol. 124, 2014, 8 pages.

Rohr, S., et al., "Slow Conduction in Cardiac Tissue, I: Effects of a Reduction of Excitability Versus a Reduction of Electrical Coupling on Microconduction," Circulation Research, Journal of the American Heart Association, vol. 83, 1998, pp. 781-794.

\* cited by examiner

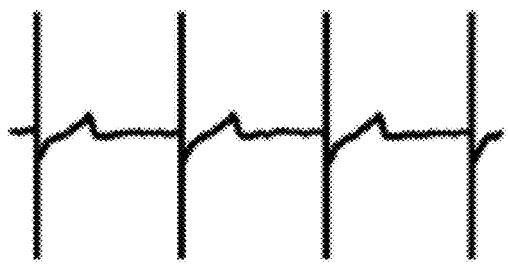
2000
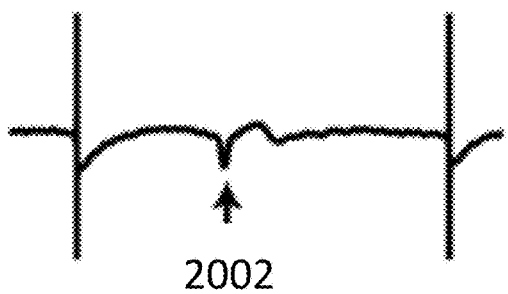
2002
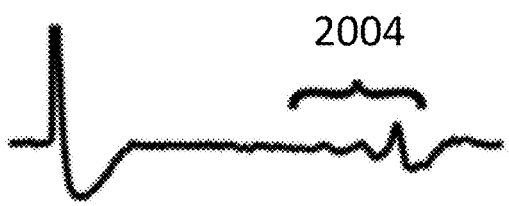
2004
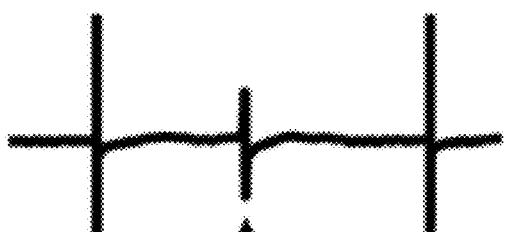
2006
Figure 20

SYSTEMS AND METHODS FOR ASSESSING DATA COLLECTED FROM AN ELECTRICALLY ACTIVE CELL CULTURE

CROSS-REFERENCE TO RELATED APPLICATIONS

This application claims the benefit of U.S. Provisional Patent Application No. 62/135,382, filed on Mar. 19, 2015, entitled "SYSTEMS AND METHODS FOR ASSESSING DATA COLLECTED FROM AN ELECTRICALLY ACTIVE CELL CULTURE," the disclosure of which is expressly incorporated herein by reference in its entirety.

BACKGROUND

The safety of candidate pharmaceutical compounds must be evaluated in pre-clinical testing prior to advancement to human clinical trials. This pre-clinical testing seeks to evaluate the safety of the compound on the various organ systems of the human body. Late stage pre-clinical testing often involves testing in animal models to assess the effects of the compound on the various organ systems. However, animal studies are expensive, and both physically and administratively labor-intensive. To ensure animal comfort and compliance with ethical standards, researchers must devise and maintain stringent animal housing and research protocols. It is therefore desirable to eliminate unsafe candidate compounds prior to reaching the animal testing phase, reducing the time and expense allotted to animal testing.

In vitro testing is often used in the earlier stages of pre-clinical testing to eliminate unsafe compounds prior to advancement to the later animal stages. For example, interconnected cellular networks of cardiomyocytes may be formed on a substrate for the testing of potential new heart therapies. Primary cardiomyocytes harvested from an animal, or animal or human stem cell-derived cardiomyocytes, form interconnected cellular networks when cultured on a cell culture substrate. The individual cardiomyocytes within a network are connected through gap junctions that allow ions to flow from one cell to another. This electrical connection allows an electrical action potential, which is first generated by a pacemaker cell, to propagate from one cell to the next.

Formation of an electrical action potential starts with a buildup of charge across a cell membrane. This buildup occurs spontaneously in cardiac cells, and more frequently in pacemaker cardiomyocytes than non-pacemaking cardiomyocytes. When the transmembrane charge reaches a threshold value, ions rush into the first cell (the depolarization phase). This triggers an action potential, which is a sharp influx of additional ions into the cytoplasm. The gap junctions distributed across the cell membrane allow ions to flow into neighboring cells, enabling the spread of the action potential.

Molecular processes within the cell tie the electrical action potential to the physical contraction of the cardiomyocytes. The propagation of the cardiac action potential across an in vitro cellular network, and the resulting contraction, resembles the propagation and contraction observed within the human heart and thus is often referred to as a "beat". Many in vitro cardiomyocyte networks exhibit spontaneous beating, where each cardiac action potential propagation (and corresponding physical beat) is followed by a brief pause and then another cardiac action potential propagation and beat.

In vitro diagnostics allow researchers to analyze non-electrical properties of many types of cells, such as cell viability, density, and proliferation rates. However, electrically active cultures, such as cardiomyocytes, enable researchers to test additional properties related to electrical activity. For example, a cardiomyocyte culture may be assessed by the gap junction distribution, or degree of electrical connectivity between cells. This property may relate to the ability of a beat to be transmitted homogenously throughout a culture.

In another example, electrical measurements taken from a cardiomyocyte give researchers an indication of the cell health, quality, and level of maturity. For example, patch-clamp techniques provide measures of the action potential of an individual cell. A patch-clamp uses an electrode inserted into the cell membrane to measure transmembrane voltage. For a healthy cell, the cardiac action potential is initiated with a depolarization phase, where sodium rushes into the cell. The depolarization phase is followed by a plateau phase, dominated by the influx of calcium, where the cells remains depolarized, and ultimately a repolarization phase characterized by an outflux of potassium and a return to the starting transmembrane potential. Patch-clamp technologies can be used to detect abnormalities in the action potential within a single cell, which may point to functional problems. However, performing testing on individual cells is difficult and time-consuming. Furthermore, cardiomyocytes may behave differently when separated from their network, thus calling experimental results into question.

Other technologies, such as impedance measurement systems, can provide information about the physical beating of the cells, but do not reveal important functional information associated with the electrical action potential. Finally, optical imaging of the network electrophysiology can be performed using secondary voltage sensitive optical reporters. However, these protocols may be time consuming and cytotoxic, eliminating the ability to perform multiple experiments on the same culture.

Microelectrode arrays (MEAs) having a plurality of microelectrodes situated within each well enable researchers to measure signals from electrically active cells cultured on their surfaces. Herein, "microelectrode" and "electrode" will be used interchangeably. Cells are cultured across the array of electrodes within a well such that signals are detected from multiple electrically active cells, such as cardiomyocytes, simultaneously. These signals, called field potential signals, may change shape in response to the addition of a candidate compound to the cardiomyocyte culture. The changes may be used to evaluate the cardiac safety risk of a compound. Additionally, these measures may be used to develop and characterize new stem cell lines, to compare the electrophysiology of the cells to in vivo signals from native cardiomyocytes, and/or to evaluate in vitro models of disease.

However, data trends relevant to the experimental question may be masked by confounding variables. For example, a beat in a culture with below average cell density may be slower than normal. This could be incorrectly interpreted as an immature developmental state in a stem cell differentiation process. Electrically active cell cultures may have spatial variability across the culture. One region of the culture may beat more frequently, or a beat may be transmitted faster in certain regions. A culture may also have temporal instability. For example, the beat period (time between beats) may increase or decrease sporadically due to environmental conditions such as, for example, changing temperature. This could lead to unreliable data if, for example, the researcher were testing a compound meant to increase heart rate.

Arrhythmia analysis for an in vitro assay according to conventional techniques consists of identifying, in a binary sense, whether an arrhythmic event has or has not occurred during a defined analysis time window. In other words, the presence or absence of drug-induced arrhythmic events is assessed (without quantification) according to conventional techniques. Recent studies have aimed to provide an analog, or graded, quantification of the arrhythmia burden induced by a test compound. For example, in a recent study, the effects of a test drug on an in vitro culture of stem cell-derived cardiomyocytes was evaluated at multiple concentrations and the number of irregular beats was counted during a fixed time window. The concentration at which 20% of the beats were irregular was compared to the clinical Cmax drug concentration to quantify arrhythmic risk. Guo, L. et al., "Refining the Human iPSC-Cardiomyocyte Arrhythmic Risk Assessment Model," *Toxicological Sciences: An Official Journal of the Society of Toxicology*, Vol. 136 (2): pp. 581-94 (2013). Additionally, in another recent study, multiple quantitative metrics of irregular beats were developed and a multi-parametric analysis was used to characterize the arrhythmic phenotype of test compounds. Gilchrist, K. H. et al., "High-Throughput Cardiac Safety Evaluation and Multi-Parameter Arrhythmia Profiling of Cardiomyocytes Using Microelectrode Arrays" *Toxicology and Applied Pharmacology*, Vol. 28(2): pp. 249-57 (2015).

SUMMARY

Disclosed herein are systems and methods for assessing data collected from an electrically active cell culture. Optionally, the data can be collected using a microelectrode array (MEA). For example, electrically active cells, such as cardiomyocytes, are cultured such that they are in electrical communication with at least a portion of the electrodes of a well of the MEA. In some implementations, the electrically active cells are cardiomyocytes and/or cardiomyocyte-like cells. In some implementations, the electrically active cells are derived from one or more of a primary cell harvest, a stem cell, or a cell line.

The assessments derived from the disclosed methods can be used to reduce the effects of confounding variables in data obtained from an electrically active cell culture. The methods can also be used to decide if a particular culture is suitable for inclusion in scientific and characterization studies. Also disclosed is a method of finding the global conduction velocity of an electrically active cell culture.

The data, such as field potential signals, are measured and collected by a plurality of electrodes. In some implementations, the data are collected by at least two electrodes and over at least two individual beats. A researcher can use the data to determine one or more parameters associated with the electrically active cell culture. The researcher can make an assessment of the electrically active cell culture based on the parameters. In some implementations, the parameters can pertain to the temporal stability or the spatial stability associated with the electrically active cell culture.

The plurality of electrodes that measure the data are in electrical communication with at least a portion of the electrically active cell culture. The plurality includes at least two electrodes. In some implementations, the plurality includes three or more electrodes. In other implementations, the plurality includes 10-10000 electrodes. The electrodes make up at least part of a microelectrode array (MEA). The MEA is communicatively coupled with an analyzer having a processor. The processor executes computer-executable instructions to determine the one or more parameters associated with the electrically active cell culture based on the data collected. The analyzer further includes a display. The processor is in communication with the display and is configured to display information associated with the one or more parameters or the data collected.

The data measured by the plurality of electrodes can be used to determine one or more parameters that are associated with the electrically active cell culture. These parameters include but are not limited to: cell density, an ion channel distribution, arrhythmogenic behaviors, early after depolarization events, cell viability, number of pacemaker regions, distribution of pacemaker regions, pacemaker region activation frequency and timing, areas of conduction block, quality of attachment to a cell culture substrate, quality of contact with the electrodes, conduction velocity, global conduction velocity, field potential duration, repolarization morphology, amplitude of the field potential signal, slope of the field potential signal, beat period, variability in beat period, and beat propagation patterns of the electrically active cell culture based on the data collected.

These aforementioned parameters can be used to gauge the quality level of the electrically active cell culture. In some implementations, the quality level can be compared to a threshold requirement for the given parameter. A researcher can make a decision to include or exclude the electrically active cell culture in scientific and characterization studies based on the quality level. These studies can include evaluation of candidate compounds prior to clinical trials, for example, human clinical trials.

In some implementations of the methods, the determined parameters can be compared to a threshold requirement for quality level. The electrically active cell culture is only included in the scientific and characterization studies if it meets or exceeds the threshold requirement. In some embodiments, a researcher can increase the quality level of the electrically active cell culture by delivering electrical stimulation to the culture via the electrodes. The electrical stimulation can improve the temporal stability or the spatial stability of the parameters.

In some implementations of the methods, beat propagation patterns are determined for use in making assessments of the electrically active cell culture. To determine a beat propagation pattern, a beat is identified within the electrically active cell culture. The beat is associated with a corresponding beat start time, beat starting location, and an adjacent beat starting electrode based on the data collected by the MEA. The transmission of the beat can be monitored as it propagates from the beat starting electrode to a beat receiving electrode. Data collected by the beat receiving electrode is used to register a beat arrival time. The difference in the beat arrival time and the beat start time is calculated as the delay time for the given beat receiving electrode. The delay times calculated for a plurality of electrodes are used to generate a multi-dimensional data array. Each point in the data array represents the delay time for an individual beat receiving electrode. The data array can be used to create a delay map of a spatial beat propagation pattern.

Implementations of the methods can also include generating a plurality of delay maps over multiple beats. Non-dominant beat propagation patterns can be identified and the associated data arrays can be eliminated from further calculations. Comparisons can be made between the first delay map and an additional delay map, and the comparison can be used to make an assessment pertaining to the spatial stability and/or the temporal stability of the beat propagation pattern. The assessment can be used to decide if the electrically active cell culture will be included in scientific and characterization studies.

In some implementations of the methods, the data are used to determine the conduction velocity of an electrical signal through the electrically active cell culture. A data array of delay times can be used to calculate the conduction velocity in more than one dimension, or in a plurality of directions simultaneously.

In some implementations, the data array of delay times is used to calculate global conduction velocity, and the global conduction velocity is used to make the assessment of the electrically active cell culture. In these implementations, a processor uses the data array of delay times to create a scatter plot of the beat propagation. The x-axis of the scatter plot represents the distance between the beat starting electrode and the beat receiving electrode, and the y-axis of the scatter plot represents the corresponding delay time. A best fit line is found through the delay times on the scatter plot. The corresponding slope of the best fit line, m, can be used to calculate the global conduction velocity. In some implementations, the best fit line is found using a least squares approach. In some implementations, the global conduction velocity is the reciprocal of the slope, m.

The assessment of the electrically active cell culture can pertain to a temporal stability of at least one of the one or more parameters, a spatial stability of at least one of the one or more parameters, or both, depending upon the particular implementation of the methods. For example, the assessment can include consideration of the coefficient of variation or the standard deviation of at least one of the parameters. The assessment can be compared to a predetermined threshold requirement, and the comparison can be used to decide if the electrically active cell culture will be included or excluded in scientific and characterization studies. In some implementations, an assessment of temporal stability can be used to detect early after depolarization events.

Some implementations of the methods for assessing an electrically active cell culture include filtering the data obtained from an electrically active cell culture. These methods include using a processor to collect field potential signals over a period of time. The field potential signals are measured by the plurality of electrodes that are in electrical communication with at least a portion of the electrically active cell culture. The electrodes are communicatively coupled with the processor.

In some implementations, methods of filtering data can include using a processor to determine the temporal stability of at least one parameter associated with the electrically active cell culture based on the data collected. The coefficient of variance or the standard deviation of the parameter over time is considered in the in the determination of temporal stability. The temporal stability is used in a decision of whether the electrically active cell culture will be included in scientific and characterization studies.

In some implementations, methods of filtering data can include using a processor to determine the spatial stability of at least one parameter associated with the electrically active cell culture based on the data collected. The determination of spatial stability accounts for a coefficient of variance or a standard deviation of the parameter at different locations within the cell culture. The spatial stability is used in a decision of whether the electrically active cell culture will be included in scientific and characterization studies.

The methods for assessing an electrically active cell culture can also include identifying abnormal electrical activity. Identifying abnormal electrical activity includes collecting, over a period of time, by a processor, field potential signals measured by a plurality of electrodes. The plurality of electrodes are in electrical communication with at least a portion of the electrically active cell culture. The plurality of electrodes are also communicatively coupled with the processor. The methods for identifying abnormal electrical activity also include determining, by the processor, a series of beat periods. A beat period is the duration of time between a first field potential signal and a second field potential signal. The methods further include comparing each beat period in the series to a predetermined threshold requirement and designating each beat period as a long beat period or a short beat period relative to the threshold requirement. The methods of identifying abnormal electrical activity further include making an assessment of abnormal electrical activity based on the relative number of long beat periods to short beat periods. In some implementations, the assessment can pertain to early after depolarization events.

Also disclosed is a system for performing the methods for assessing an electrically active cell culture using a MEA. The system includes a plurality of electrodes. At least a portion of the plurality of electrodes are in electrical communication with at least a portion of an electrically active cell culture. The system also includes an analyzer having a processor. The processor is communicatively coupled with the plurality of electrodes and is configured to execute computer-readable instructions. The computer-readable instructions include instructions to at least 1) collect data measured by the plurality of electrodes, and 2) determine at least one or more parameters associated with the electrically active cell culture based on the data collected. An assessment can be made of the electrically active cell culture based on the one or more determined parameters. The data collected can be, for example, field potential signals.

The processor can be configured to deliver electrical stimulation to the electrically active cell culture via at least one of the plurality of electrodes. The electrical stimulation can improve a temporal stability of a beat propagation pattern, a spatial stability of a beat propagation pattern, or both.

In some implementations, the processor is configured to determine at least one or more parameters associated with temporal stability or spatial stability associated with the electrically active cell culture based on the data collected.

In some implementations, the processor is configured to calculate a delay time between the beat arrival time and the beat start time.

Some implementations of the system further include a memory. The processor can be configured to generate a multi-dimensional data array of the delay times for a plurality of electrodes around the beat starting electrode. Each point in the data array represents the delay time for an individual beat receiving electrode. The data array is stored in the memory. In some implementations, the processor is configured to generate a first delay map of a spatial beat propagation pattern using the data array of delay times.

In other implementations, the processor is configured to generate a plurality of delay maps for multiple beats and identify any non-dominant beat propagation patterns in the electrically active cell culture. The processor can further be configured to eliminate the data arrays associated with non-dominant beat propagation patterns from further calculations. The processor can also be configured to make a comparison between a first delay map and an additional delay map, and use the comparison in making an assessment. The assessment can pertain to at least one of the spatial stability and the temporal stability of the beat propagation pattern.

In some implementations, the processor is configured to determine the conduction velocity. The data array of delay times is used by the processor to calculate the conduction velocity of an electrical signal through the cell culture. In some implementations, the processor is configured to measure conduction velocity in a plurality of directions simultaneously, or in more than one dimension.

In some implementations, the processor is configured to calculate a global conduction velocity for an electrically active cell culture, and the global conduction velocity is used to make the assessment of the electrically active cell culture. The assessment of the electrically active cell culture can pertain to a temporal stability of at least one parameter, a spatial stability of at least one parameter, or both.

An example electrophysiology culture system is described herein. The system can include a sensor (e.g., one or more electrodes, photosensors, etc.) configured to record a physiological signal from an electrically active cell culture, and an analyzer having a processor that is communicatively coupled with the sensor. The processor can be configured to execute computer-readable instructions that cause the processor to receive the physiological signal recorded by the sensor, analyze the physiological signal to determine a beat period associated with the electrically active cell culture and a pro-arrhythmic indicator, and determine a quantitative measure of arrhythmia burden. The quantitative measure of arrhythmia burden can be a relationship between the beat period associated with the electrically active cell culture and the pro-arrhythmic indicator.

Additionally, determining a pro-arrhythmic indicator can include determining a percentage (or a ratio) of beats exhibiting the pro-arrhythmic indicator. For example, the quantitative measure of arrhythmia burden can a specific beat period associated with the electrically active cell culture at which a predetermined percentage of beats exhibit the pro-arrhythmic indicator (e.g., EAD50, EAD20).

Alternatively or additionally, the sensor can be at least one electrode further configured to deliver electrical stimulation to the electrically active cell culture. The processor can be configured to execute further computer-readable instructions that cause the processor to control the beat period associated with the electrically active cell culture using electrical stimulation.

Alternatively or additionally, the system can include at least one light-emitting element configured to deliver optogenetic stimulation to the electrically active cell culture. The processor can be configured to execute further computer-readable instructions that cause the processor to control the beat period associated with the electrically active cell culture using optogenetic stimulation.

Alternatively or additionally, the processor can be configured to execute further computer-readable instructions that cause the processor to generate a curve that defines the relationship between the beat period associated with the electrically active cell culture and the percentage of beats exhibiting the pro-arrhythmic indicator. Optionally, the quantitative measure of arrhythmia burden can be a characteristic of the curve (e.g., a slope and/or amplitude).

Alternatively or additionally, determining a pro-arrhythmic indicator can include detecting a region of beat period bi-stability by estimating a probability distribution of beat period. The region of beat period bi-stability can be a plurality of beats with a bimodal probability distribution of beat period. Optionally, the probability distribution of beat period can be estimated using kernel density estimation. The plurality of beats with the bimodal probability distribution can be a set of beats having a short beat period and a set of beats having a long beat period. Optionally, detecting a region of beat period bi-stability can include classifying each of a plurality of beats as having a short beat period or a long beat period. Optionally, the processor can be configured to execute further computer-readable instructions that cause the processor to determine a quantitative measure of arrhythmia burden based on the number of beats classified as having the long beat period.

Alternatively or additionally, the processor can be configured to execute further computer-readable instructions that cause the processor to identify a predetermined number of consecutive beats having maximum stability. The quantitative measure of arrhythmia burden can be determined based on the predetermined number of consecutive beats having maximum stability. Additionally, identifying a predetermined number of consecutive beats having maximum stability can include estimating a coefficient of variation of beat period. The coefficient of variation can be the measure of stability.

Alternatively or additionally, the quantitative measure can be used to assess the safety of a pharmaceutical compound in contact with the electrically active cell culture.

Alternatively or additionally, the physiological signal can be a cardiac beat signal. The cardiac beat signal can include at least one of a field potential signal, an impedance signal, an action potential signal, a calcium signal, an optical signal, or combinations thereof.

Alternatively or additionally, the pro-arrhythmic indicator can be an early after depolarization (EAD) event. The pro-arrhythmic indicator can be other events including, but not limited to, a rolling EAD, ectopic beat, and/or tachyarrhythmia.

Alternatively or additionally the electrically active cell culture can be an in vitro cell culture.

An example method for quantifying an arrhythmia burden is also described herein. The method can include recording a physiological signal from an electrically active cell culture; analyzing the physiological signal to determine a beat period associated with the electrically active cell culture and a pro-arrhythmic indicator; and determining a quantitative measure of arrhythmia burden. The quantitative measure of arrhythmia burden can be a relationship between the beat period associated with the electrically active cell culture and the pro-arrhythmic indicator.

Additionally, determining a pro-arrhythmic indicator can include determining a percentage (or a ratio) of beats exhibiting the pro-arrhythmic indicator. For example, the quantitative measure of arrhythmia burden can a specific beat period associated with the electrically active cell culture at which a predetermined percentage of beats exhibit the pro-arrhythmic indicator (e.g., EAD50, EAD20).

Alternatively or additionally, the method can further include controlling the beat period associated with the electrically active cell culture using at least one of electrical stimulation, optogenetic stimulation, or temperature.

Alternatively or additionally, the method can further include generating a curve that defines the relationship between the beat period associated with the electrically active cell culture and the percentage of beats exhibiting the pro-arrhythmic indicator. Optionally, the quantitative measure of arrhythmia burden can be a characteristic of the curve (e.g., a slope and/or amplitude).

Alternatively or additionally, the method can further include maintaining the beat period associated with the electrically active cell culture at a fixed beat period; and contacting a pharmaceutical compound with the electrically active cell culture. The quantitative measure of arrhythmia burden can be a concentration of the pharmaceutical compound that induces a predetermined percentage of beats exhibiting the pro-arrhythmic indicator.

Alternatively or additionally, determining a pro-arrhythmic indicator can include detecting a region of beat period bi-stability by estimating a probability distribution of beat period. The region of beat period bi-stability can be a plurality of beats with a bimodal probability distribution of beat period. Optionally, the probability distribution of beat period can be estimated using kernel density estimation. The plurality of beats with the bimodal probability distribution can be a set of beats having a short beat period and a set of beats having a long beat period. Optionally, detecting a region of beat period bi-stability can include classifying each of a plurality of beats as having a short beat period or a long beat period. Optionally, the processor can be configured to execute further computer-readable instructions that cause the processor to determine a quantitative measure of arrhythmia burden based on the number of beats classified as having the long beat period.

Alternatively or additionally, the method can further include identifying a predetermined number of consecutive beats having maximum stability. The quantitative measure of arrhythmia burden can be determined based on the predetermined number of consecutive beats having maximum stability. Additionally, identifying a predetermined number of consecutive beats having maximum stability can include estimating a coefficient of variation of beat period. The coefficient of variation can be the measure of stability.

Alternatively or additionally, the method can further include contacting a pharmaceutical compound with the electrically active cell culture.

Alternatively or additionally, the method can further include assessing the safety of the pharmaceutical compound based on the quantitative measure.

Alternatively or additionally, the physiological signal can be a cardiac beat signal. The cardiac beat signal can include at least one of a field potential signal, an impedance signal, an action potential signal, a calcium signal, an optical signal, or combinations thereof.

Alternatively or additionally, the pro-arrhythmic indicator can be an early after depolarization (EAD) event. The pro-arrhythmic indicator can be other events including, but not limited to, a rolling EAD, ectopic beat, and/or tachyarrhythmia.

Alternatively or additionally the electrically active cell culture can be an in vitro cell culture.

Another electrophysiology culture system is described herein. The system can include a sensor (e.g., one or more electrodes, photosensors, etc.) configured to record a physiological signal from an electrically active cell culture, and an analyzer having a processor that is communicatively coupled with the sensor. The processor can be configured to execute computer-readable instructions that cause the processor to receive the physiological signal recorded by the sensor, analyze the physiological signal to determine a beat period associated with the electrically active cell culture, detect a region of beat period bi-stability, and identify one or more beats exhibiting a pro-arrhythmic indicator within the region of beat period bi-stability.

An example method for identifying one or more beats exhibiting a pro-arrhythmic indicator is described herein. The method can include recording a physiological signal from an electrically active cell culture; analyzing the physiological signal to determine a beat period associated with the electrically active cell culture; detecting a region of beat period bi-stability; and identifying the one or more beats exhibiting the pro-arrhythmic indicator within the region of beat period bi-stability.

Alternatively or additionally, detecting a region of beat period bi-stability can include estimating a probability distribution of beat period. The region of beat period bi-stability can be a plurality of beats with a bimodal probability distribution of beat period. Optionally, the probability distribution of beat period can be estimated using kernel density estimation. The plurality of beats with the bimodal probability distribution can be a set of beats having a short beat period and a set of beats having a long beat period. Optionally, detecting a region of beat period bi-stability can include classifying each of a plurality of beats as having a short beat period or a long beat period. Optionally, the processor can be configured to execute further computer-readable instructions that cause the processor to determine a quantitative measure of arrhythmia burden based on the number of beats classified as having the long beat period.

Alternatively or additionally, the method can further include generating an average short beat period from one or more beats classified as having the short beat period. Alternatively or additionally, the method can further include generating an average long beat period from one or more beats classified as having the long beat period. Optionally, the method can further determining a quantitative measure of arrhythmia burden based on at least one of the average short beat period or the average long beat period.

Alternatively or additionally, the method can further include assessing the safety of the pharmaceutical compound in contact with the electrically active cell culture based on the quantitative measure.

Alternatively or additionally, the physiological signal can be a cardiac beat signal. The cardiac beat signal can include at least one of a field potential signal, an impedance signal, an action potential signal, a calcium signal, an optical signal, or combinations thereof.

Alternatively or additionally, the pro-arrhythmic indicator can be an early after depolarization (EAD) event. The pro-arrhythmic indicator can be other events including, but not limited to, a rolling EAD, ectopic beat, and/or tachyarrhythmia.

Alternatively or additionally the electrically active cell culture can be an in vitro cell culture.

Yet another electrophysiology culture system is described herein. The system can include a sensor (e.g., one or more electrodes, photosensors, etc.) configured to record a physiological signal from an in vitro electrically active cell culture, and an analyzer having a processor that is communicatively coupled with the sensor. The processor can be configured to execute computer-readable instructions that cause the processor to receive the physiological signal recorded by the sensor, analyze the physiological signal to determine a beat period associated with the in vitro electrically active cell culture, identify a predetermined number of consecutive beats having maximum stability, and determine a quantitative measure of cardiac beating based on the predetermined number of consecutive beats having maximum stability.

An example method for assessing electrically active cell culture data is described herein. The method can include recording a physiological signal from an in vitro electrically active cell culture; analyzing the physiological signal to determine a beat period associated with the in vitro electrically active cell culture; identifying a predetermined number of consecutive beats having maximum stability, and determining a quantitative measure of cardiac beating based on the predetermined number of consecutive beats having maximum stability. The quantitative measure of cardiac beating can include, but is not limited to, beat period, field potential duration (FPD), depolarization spike amplitude, or conduction velocity.

Optionally, the predetermined number of consecutive beats having maximum stability can be between about 5 and about 500 consecutive beats. For example, the predetermined number of consecutive beats having maximum stability can be about 30 consecutive beats. It should be understood that about 30 consecutive beats is provided only as an example and that the predetermined number of consecutive beats having maximum stability can be more or less than about 30 beats.

Alternatively or additionally, the method can further include estimating a coefficient of variation of beat period. The predetermined number of consecutive beats having maximum stability can be identified using the coefficient of variation of beat period. For example, the predetermined number of consecutive beats having maximum stability have relatively lowest coefficients of variation of beat period. Optionally, the method can further include excluding from the determination of the quantitative measure of arrhythmia burden a plurality of consecutive beats with relatively high coefficients of variation of beat period. It should be understood that the coefficient of variation is provided only as an example stability metric. In other words, the coefficient of variation is provided as only one example of a statistical measure of a collection of beat periods. This disclosure contemplates that other stability metrics (e.g., standard deviation) can be used with the techniques described herein.

Alternatively or additionally, the method can further include assessing the safety of a pharmaceutical compound in contact with the in vitro electrically active cell culture based on the quantitative measure of cardiac beating.

Alternatively or additionally, the physiological signal can be a cardiac beat signal. The cardiac beat signal can include at least one of a field potential signal, an impedance signal, an action potential signal, a calcium signal, an optical signal, or combinations thereof.

Another electrophysiology culture system is described herein. The system can include a plurality of sensors configured to record a physiological signal from an electrically active cell culture; and an analyzer having a processor that is communicatively coupled with the plurality of sensors. The processor can be configured to execute computer-readable instructions that cause the processor to receive the physiological signal recorded by the sensors, analyze the physiological signal to determine beat timings associated with the electrically active cell culture, generate a propagation pattern from respective beat timings for the same beat recorded by the plurality of sensors, and using the propagation pattern, determining whether the electrically active cell culture exhibits stable or unstable beat propagation. The plurality of sensors can be a plurality of electrodes and/or photosensors (e.g., an array of electrodes and/or photosensors).

Another example method for assessing electrically active cell culture data is described herein. The method can include recording a physiological signal from an electrically active cell culture using a plurality of sensors; analyzing the physiological signal to determine beat timings associated with the electrically active cell culture; generating a propagation pattern from respective beat timings for the same beat recorded by the plurality of sensors; and, using the propagation pattern, determining whether the electrically active cell culture exhibits stable or unstable beat propagation.

Additionally, the method can further include determining a quantitative measure of beat propagation stability using the propagation pattern.

Optionally, the propagation pattern comprises a spatial propagation pattern. Alternatively or additionally, the method can further include generating a respective spatial propagation pattern from respective beat timings for each of a plurality of beats recorded by the plurality of sensors. The quantitative measure can be a number of different respective spatial propagation patterns. Additionally, the respective spatial propagation patterns can include a dominant propagation pattern, which is the spatial propagation pattern with the most occurrences across the plurality of beats (e.g., the most common spatial propagation pattern among the generated propagation patterns). The quantitative measure can be determined based on the dominant propagation pattern. For example, the quantitative measure can be a percentage of the plurality of beats following the dominant propagation pattern. For example, the quantitative measure can be ratio of the respective propagation patterns following the dominant propagation pattern to the total number of respective propagation patterns.

Alternatively or additionally, the quantitative measure of beat propagation stability can be a conduction velocity. Optionally, the propagation pattern can be a plot of respective delay times versus respective distances for each of the plurality of sensors. A respective distance can be a distance between an origin sensor (e.g., an origin electrode) and a respective sensor (e.g., a respective electrode), and a respective delay time can be a difference between a recorded beat time at the origin sensor and a recorded beat time at the respective sensor (e.g., which is spaced apart from the origin sensor). Alternatively or additionally, the method can further include determining the respective delay times for each of the plurality of sensors. Alternatively or additionally, the method can further include performing a least squares regression on the plot of respective delay times versus respective distances for each of the plurality of sensors to determine a best fit line. The conduction velocity can be an inverse slope of the best fit line.

Alternatively or additionally, the method can further include controlling the propagation pattern associated with the electrically active cell culture using at least one of electrical stimulation, optogenetic stimulation, or temperature.

Alternatively or additionally, the method can further include assessing the safety of a pharmaceutical compound in contact with the electrically active cell culture based on the quantitative measure.

Alternatively or additionally, the electrically active cell culture can be an in vitro cell culture.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

DESCRIPTION OF DRAWINGS

FIG. 20 illustrates example types of arrhythmic events.

DETAILED DESCRIPTION

The following description of certain examples of the inventive concepts should not be used to limit the scope of the claims. Other examples, features, aspects, embodiments, and advantages will become apparent to those skilled in the art from the following description, which is by way of illustration, one of the best modes contemplated for carrying out the inventive concepts. As will be realized, the device and/or methods are capable of other different and obvious aspects, all without departing from the spirit of the inventive concepts. For example, the disclosed methods can be applied to other technologies used to monitor electrically active cell cultures without departing from the spirit of the inventive concepts. Accordingly, the drawings and descriptions should be regarded as illustrative in nature and not restrictive.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

Figure 1:
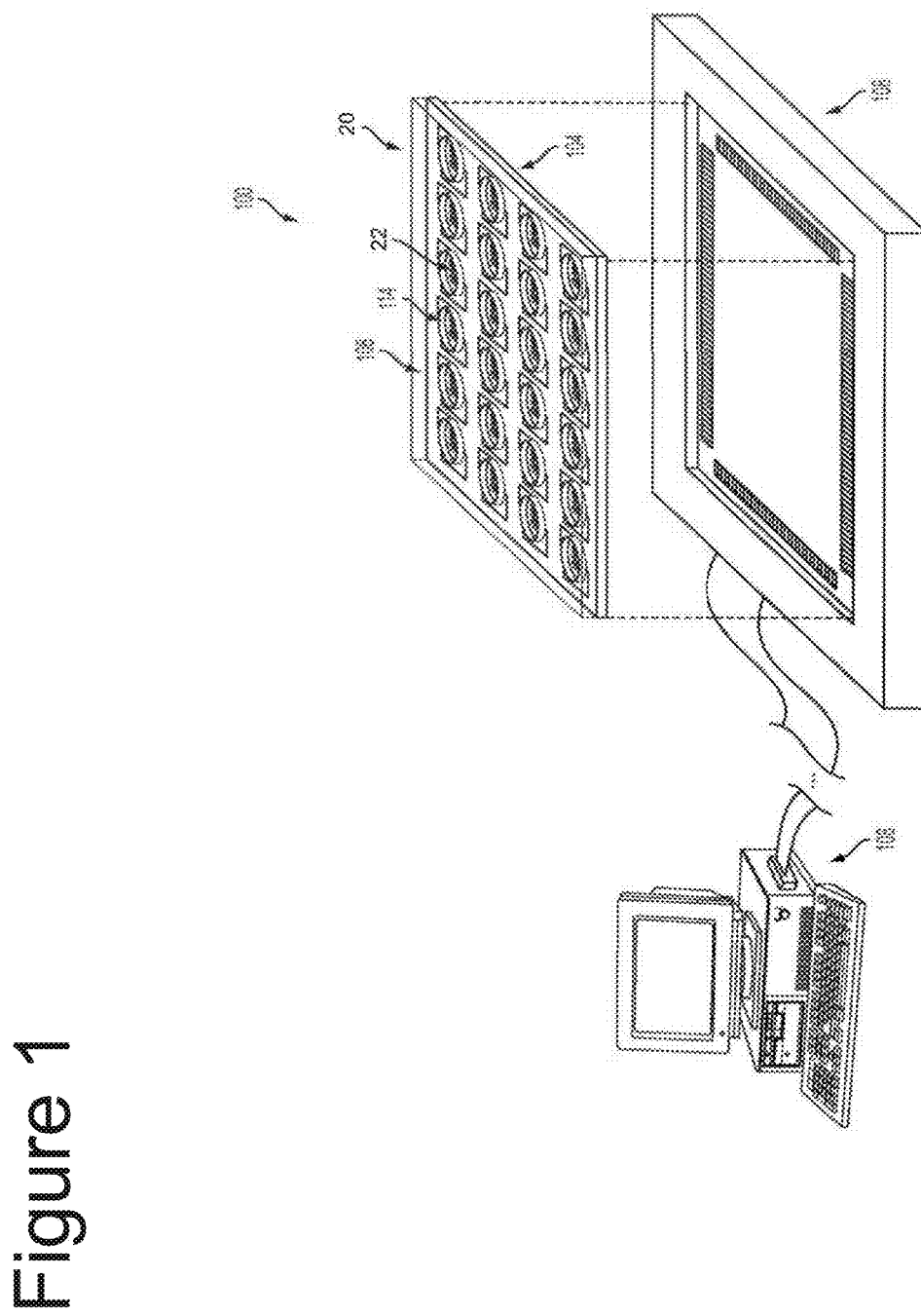
FIG. 1 is a high-throughput electrophysiology culture system including a microelectrode array (MEA).

Disclosed herein are methods of collecting data from an electrically active cell culture using a microelectrode array (MEA). Generally, an MEA is comprised of one or more wells, each well further comprising a plurality of electrodes. FIG. 1 illustrates an implementation of one exemplary aspect of a high-throughput electrophysiology culture system 100 that can be used for the systems and methods described herein. In FIG. 1, an electrophysiology culture plate, or MEA, 20 can comprise, for example, a monolithic MEA plate 104 integrated with a biologic culture plate 106, and the system 100 can further comprise electronics 108 together with software configured to stimulate a cell culture via the electrophysiology culture plate to evoke a response and to record data. The electrophysiology culture plate 20 can comprise a plurality of culture wells 114 configured to culture electroactive cells (or electrically active cells). An array of microelectrodes 22 configured to extracellularly interface with the cultured cells is operatively associated with each culture well 114. Each electrode 22 is also communicatively coupled with the electronics 108. Each electrode 22 can be configured to record electrical activity from a cell culture located within a well 114 and also to electrically stimulate those cells. This technique can provide an extracellular, label free method for examining both individual cellular behavior and overall network activity, optionally, simultaneously. Additional information regarding one type of MEA culture plates that are suitable for using in the methods and systems described herein can be found in U.S. Pre-Grant Publication No. 20150027885 by Rajaraman et al., filed on Jul. 26, 2014 and published on Jan. 29, 2015, entitled "Devices, Systems and Methods for High-Throughput Electrophysiology," which is hereby incorporated by reference in its entirety. Such high-throughput culture plates can have well counts of, for example and without limitation, 12, 24, 48, 96, 192, 384, 768, etc. Alternatively or additionally, the system 100 can optionally be configured to deliver optogenetic stimulation to the electroactive cells. For example, the system 100 can further include a respective light emitting element set corresponding to each of the plurality of culture wells 114. Additional information regarding a system suitable for delivering optogenetic stimulation can be found in U.S. Pre-Grant Publication No. 20150362476 by Clements et al., filed on Jun. 12, 2015 and published on Dec. 17, 2015, entitled "Multiwell Microelectrode Array with Optical Stimulation," which is hereby incorporated by reference in its entirety. Alternatively or additionally, the system 100 can optionally include heating and/or cooling elements configured for controlling/adjusting the temperature of the plurality of culture wells 114. Further, each well plate can have an area of interest, e.g. an electroactive area that can be, for example and without limitation, about 1.25 mm to 2 mm in diameter. Suitable MEA systems can be obtained, for example from Axion Biosystems (Atlanta, Ga., USA). Alternatively or additionally, the system 100 can be configured to collect data from an electrically active cell culture using an imaging system. For example, microscopy imaging systems for visualizing cell structures and biological processes are known in the art. This disclosure contemplates that a microscopy imaging system can be used to collect data from an electrically active cell culture.

The data from the electrically active cell culture obtained using a microelectrode array (MEA) can be used to determine parameters that assist in making assessments of the electrically active cell culture. Electrically active cells, such as cardiomyocytes, are cultured such that they are in electrical communication with at least a portion of the electrodes in a well of the MEA. The assessments derived from the disclosed methods can be used to reduce the effects of confounding variables in data obtained from an electrically active cell culture. The methods can also be used to decide if a particular culture is suitable for inclusion in scientific and characterization studies. Also disclosed is a method of finding the global conduction velocity of an electrically active cell culture.

Cardiomyocytes or cardiomyocyte-like cells can be derived from primary tissue harvests, from cell lines, from stem cells, or from cellular reprogramming protocols. The term "cardiomyocyte-like" is used to describe cells that have certain aspects in common with cardiomyocytes present in actual heart tissue. For example, like cardiomyocytes, cardiomyocyte-like cells can beat and transmit electrical signals to neighboring cells via gap junctions. The methods described herein use the term cardiomyocyte. However, the methods can be also performed using cardiomyocyte-like cell cultures or other electrically active cell cultures.

Figure 2:
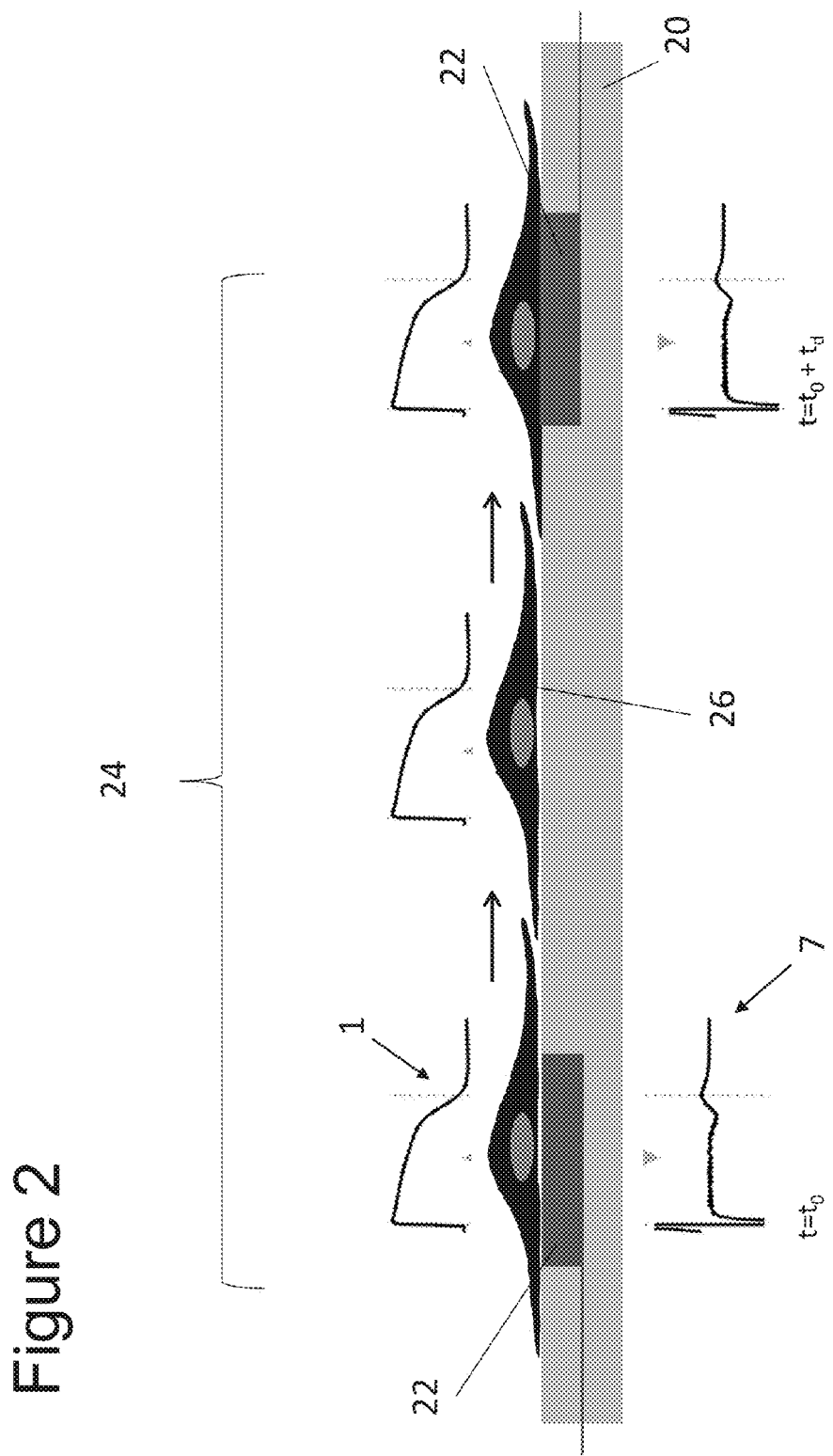
FIG. 2 is a cross-sectional schematic of electrically active cells cultured on an MEA.
Figure 3:
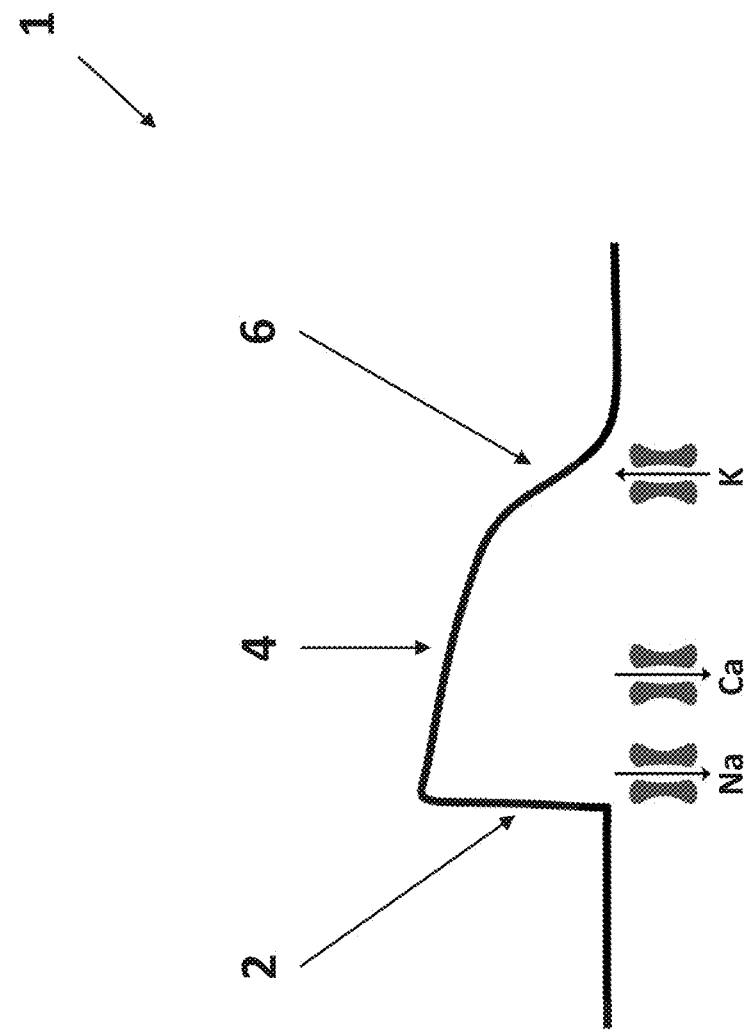
FIG. 3 is a graph of an exemplary cardiomyocyte action potential.

FIG. 2 shows cardiomyocytes 26 cultured within a well of an MEA 20. Some of the cardiomyocytes 26 are in contact with electrodes 22, which are configured to detect extracellular changes in the field potential. As shown in FIG. 3, a cardiomyocyte action potential 1 is initiated with a depolarization phase 2, where sodium rushes into the cell. The depolarization phase is followed by a plateau phase 4, dominated by the influx of calcium, where the cells remains depolarized, and ultimately a repolarization phase 6 characterized by an outflux of potassium and a return to the starting transmembrane potential.

Figure 4:
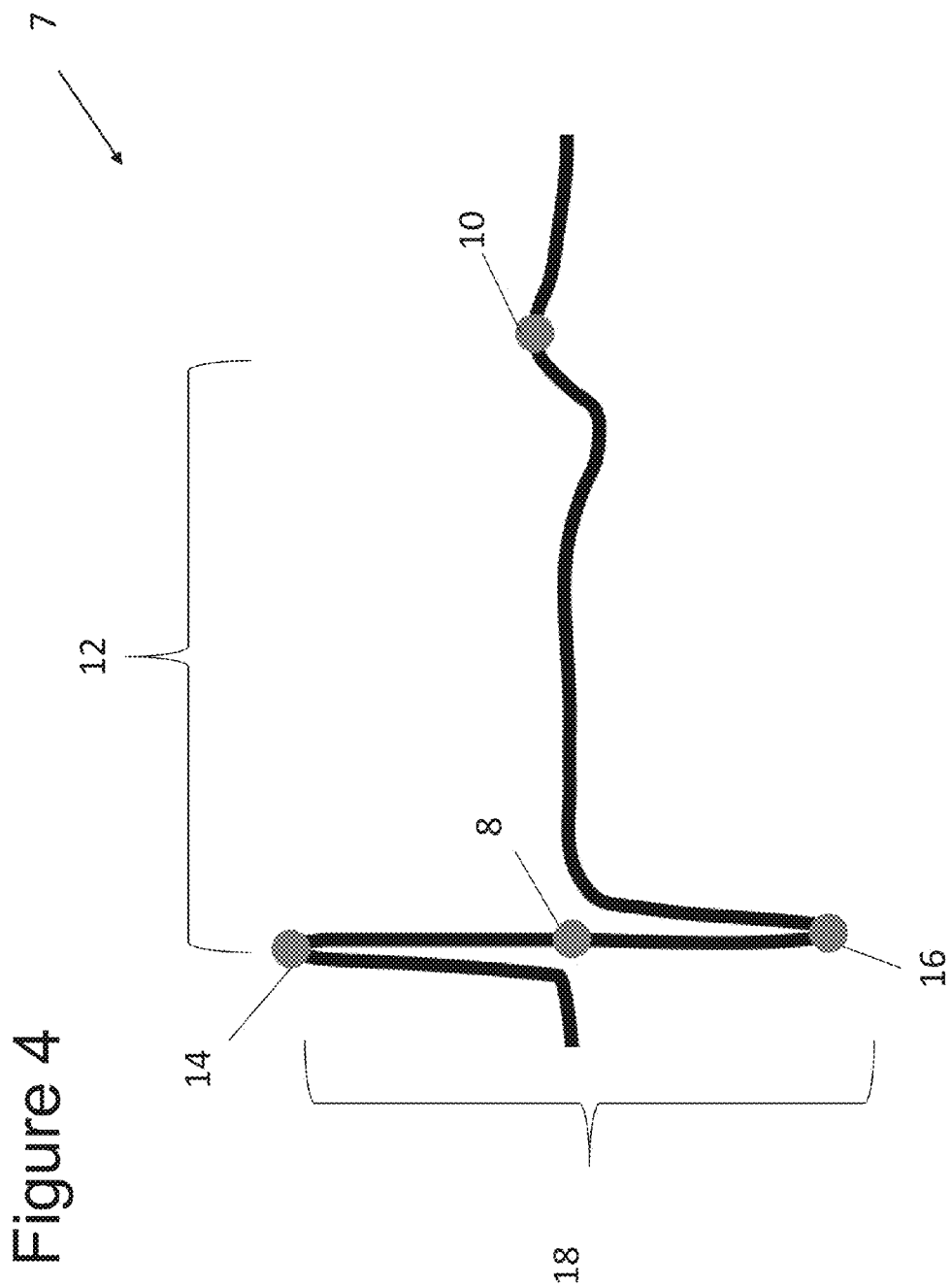
FIG. 4 is a graph of an exemplary field potential signal detected by an electrode of a MEA.
Figure 5:
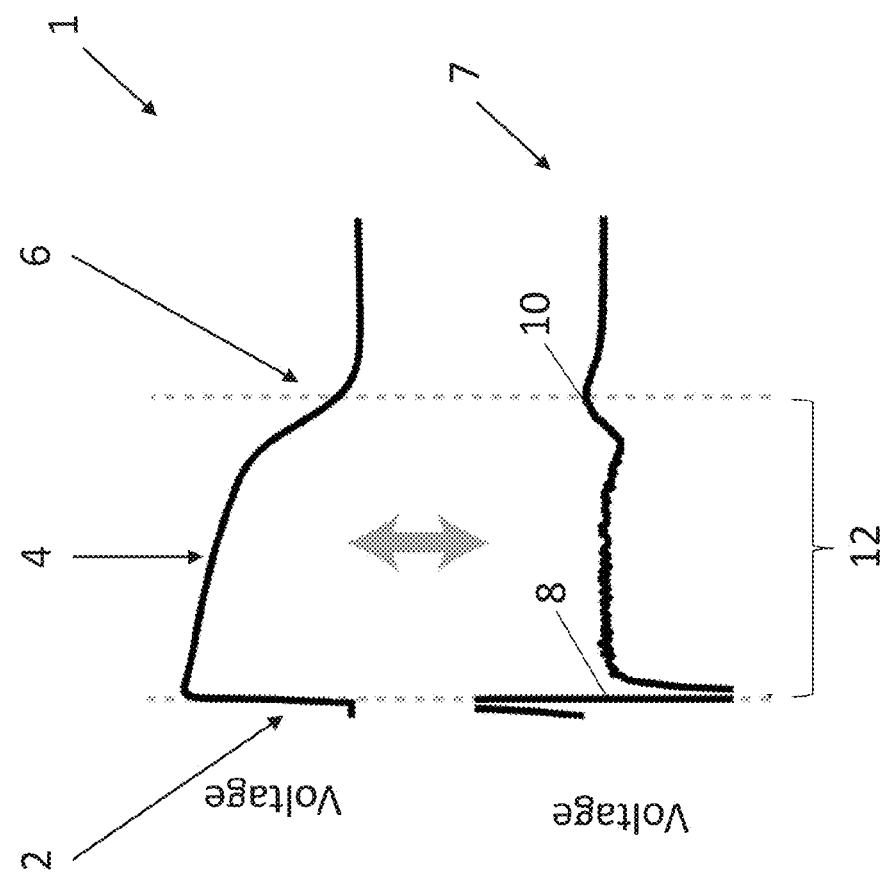
FIG. 5 is a side-by-side comparison of an exemplary cardiomyocyte action potential and the corresponding field potential signal.

Referring back to FIG. 2, the signal captured by the electrodes 22 of an MEA 20 in contact with the cellular network 24 is referred to as the field potential 7. As seen in FIG. 4, the field potential contains functional markers that represent the depolarization and repolarization of the cardiac action potential. FIG. 5 demonstrates the temporal relationship between the action potential 1 and the field potential, 7, that is measured by the electrodes of the MEA. The depolarization phase 2 is detected by the biphasic signal generated by the influx of sodium crossing a threshold. The depolarization time 8 is marked in time when the field potential signal trace hits its maximum slope. The field potential signal can also be characterized by its amplitude 18, as shown in FIG. 4. The amplitude is the difference in voltage between the depolarization peak 14 and the depolarization trough 16. The repolarization phase is marked by the peak of the T-wave 10 that follows the depolarization phase. The T-wave corresponds to the influx of potassium back into the cell and the return to the starting transmembrane potential. The field potential duration (FPD) 12, is measured as the difference between the depolarization time 8 and the peak of the T-wave 10. The beat period is the time from one depolarization 8 to the next. The relative timing of the depolarization 8 across the MEA enables the computation of a conduction velocity measurement.

Figure 6A:
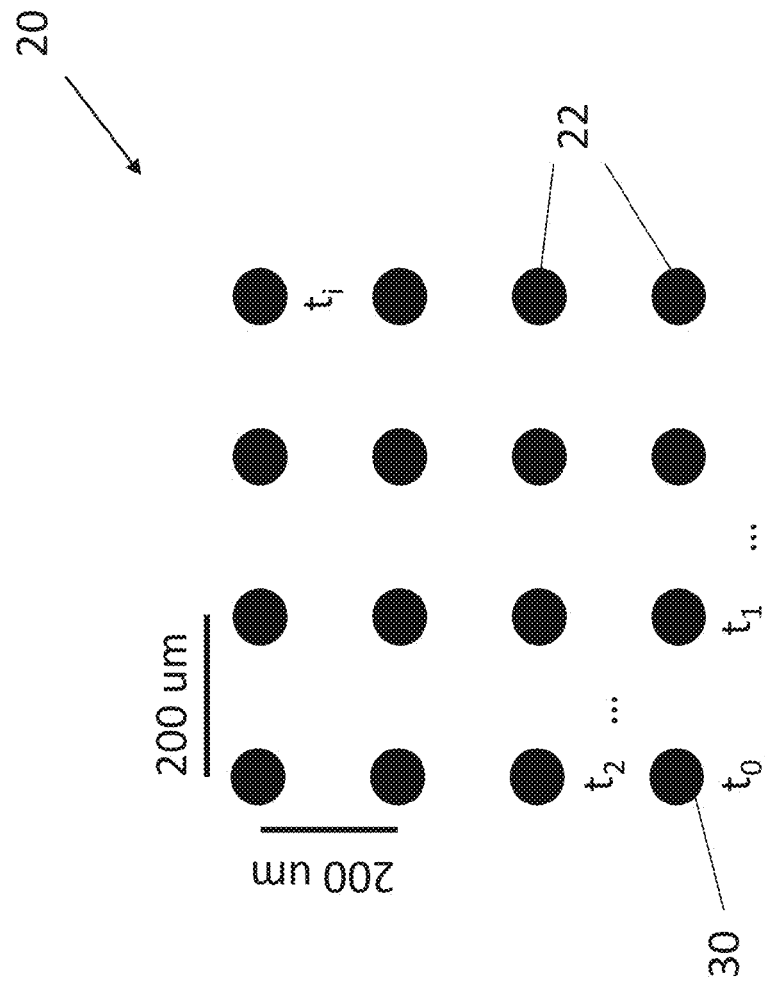
FIG. 6A is a schematic of an exemplary microelectrode array, as viewed from the top.

The beat timestamp is measured for each beat on each electrode in the array 20. Beats detected on individual electrodes 22 can be grouped into well-wide beats, based on the timestamp registered by each electrode. A single well-wide beat is expected to manifest as a single depolarization spike occurring on each electrode in very close proximity in time (for example, within 30 ms). FIG. 6A is a representation of an array of electrodes 22 of an exemplary well of a MEA 20 having electrodes 22 spaced 200 μm from one another in the vertical and horizontal directions. It is to be appreciated that the number of electrodes 22 and

TABLE 1

| Column | 1 | 2 | 3 | 4 | 5 | 6 | 7 | 8 |
|---|---|---|---|---|---|---|---|---|
| Row | | | | | | | | |
| 8 | 3.6327 | 3.6964 | 3.78702 | 4.18841 | 4.37683 | 4.67548 | 5.17479 | 5.66754 |
| 7 | NaN | 2.9467 | 3.11522 | 3.30799 | 3.64539 | NaN | 4.53261 | 5.05423 |
| 6 | 2.35768 | 2.20678 | 2.42413 | 2.54364 | 2.94875 | 3.33247 | NaN | 4.55266 |

TABLE 1-continued

| Column | 1 | 2 | 3 | 4 | 5 | 6 | 7 | 8 |
|---|---|---|---|---|---|---|---|---|
| 5 | 1.62226 | 1.53979 | 1.66882 | 2.00895 | 2.2531 | 2.79953 | 3.24352 | 4.08216 |
| 4 | 0.85232 | 0.83772 | 1.08154 | 1.32714 | 1.92559 | 2.50316 | 2.99534 | 3.72355 |
| 3 | 0.32801 | 0.33066 | 0.56054 | 1.00057 | 1.56233 | 2.37925 | 2.75342 | 3.37616 |
| 2 | 0 | 0.32583 | 0.39601 | 0.89373 | 1.34638 | 2.02139 | 2.58265 | 3.32552 |
| 1 | 0.32329 | 0.36746 | 0.43794 | 0.70659 | 1.19332 | 1.93906 | 2.52624 | 3.24036 | the spacing shown in FIG. 6A are for example purposes only and greater or fewer electrodes 22 can be used and the spacing can also differ from what is shown. As shown in FIG. 6A, the electrode that first detected the beat is considered the beat starting electrode 30. The beat timestamps, or arrival times, on the neighboring beat receiving electrodes can be used to generate a data array of delay times, as shown in Table 1. Table 1 shows an exemplary data array of delay times registered across the electrodes 22 of a well of an MEA 20. For the exemplary beat shown in Table 1, the beat starting electrode 30 is represented by the data point in column 1, row 2. The delay time ($t_{di}$) at each electrode 22 is the difference between the beat arrival time ($t_i$) on that particular beat receiving electrode 22 and the beat start time, $t_0$, at the beat starting electrode 30.

$$t_{di} = t_i - t_0$$

Figure 6B:
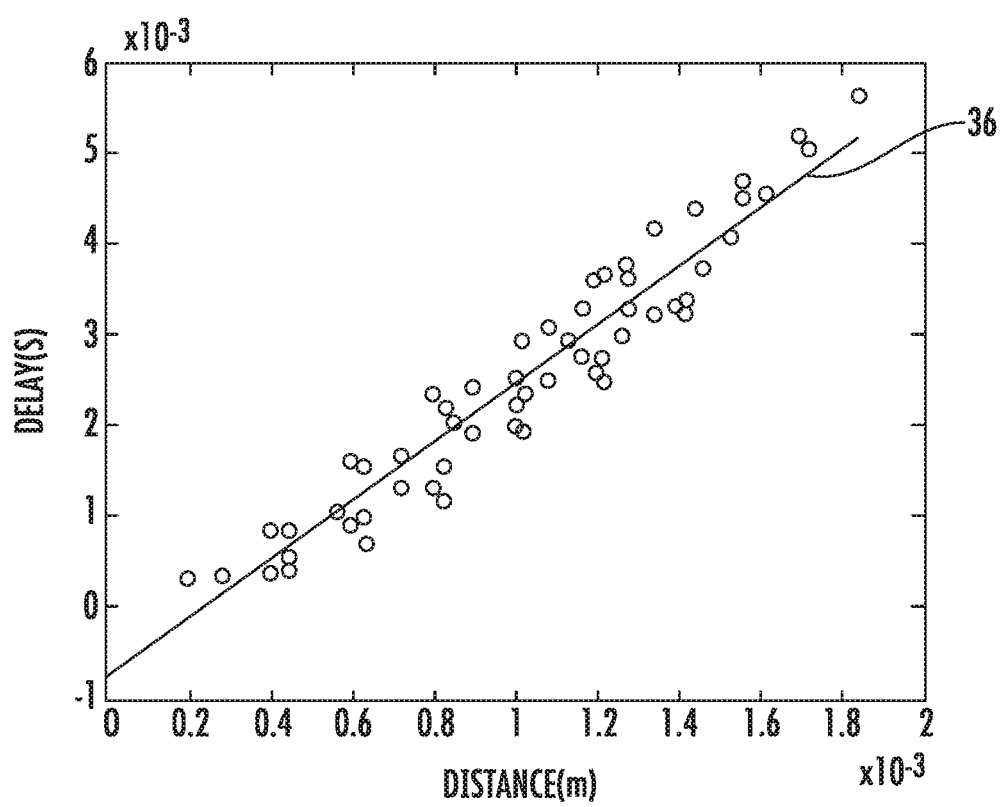
FIG. 6B is an exemplary scatter plot of delay times obtained from an MEA. The distance a beat travels from a starting electrode to a receiving electrode is graphed along the x-axis, and the time a beat takes to travel the distance is graphed along the y-axis.

The velocity at which a beat propagates through the cellular network, or the conduction velocity, is a useful parameter for assessing a cardiomyocyte culture. However, the conduction velocity can vary depending upon the location within the cell culture, and thus it is another example of a parameter that is subject to spatial variability. A data array of delay times, such as the one shown in Table 1, can be used to calculate a global conduction velocity (GCV) that is representative for the entire cell culture. The data array can be presented, for example, as a scatter plot, as shown in FIG. 6B. The X-axis of the plot is the distance between the beat starting electrode and the beat receiving electrode. The Y-axis is the corresponding delay time at the beat receiving electrode. The GCV is found by taking the slope of the best fit line 36 through the cloud of data points. For example, consider a well containing the propagation delays shown in Table 1. The electrodes 22 are spaced 200 um apart (center-to-center), as shown in FIG. 6A. Each delay value is plotted against its respective distance from the beat origin, as shown in FIG. 6B. A line is fit through the points (y=mx+c), and the slope of this line can be found by minimizing the sum of the squared errors, which occurs when $$m = \frac{\sum_{i=1}^{N}(x_i - \bar{x})(y_i - \bar{y})}{\sum_{i=1}^{N}(x_i - \bar{x})^2}$$

The reciprocal of the slope of this line is the global conduction velocity, reported in distance/time.

Figure 7A:
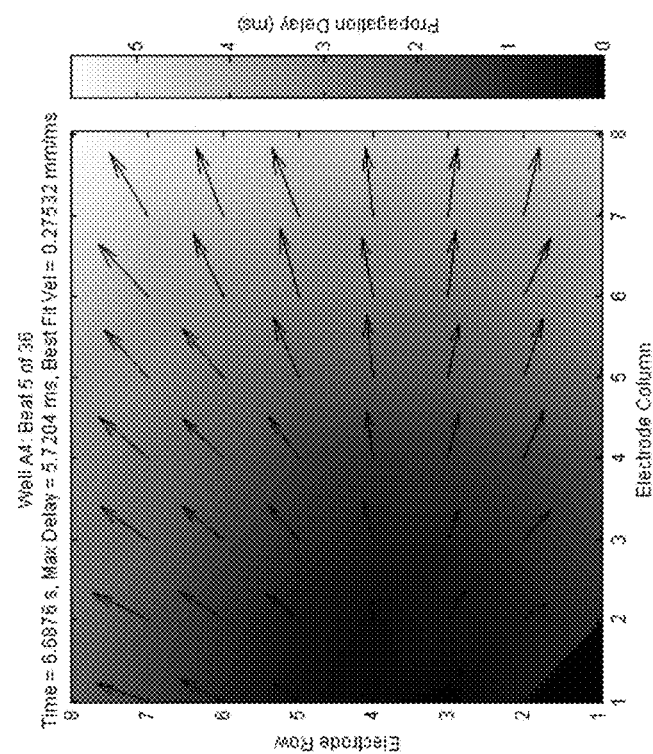
FIG. 7A is an exemplary map of a beat propagation pattern, depicting a beat that started on the edge of a culture.
Figure 7B:
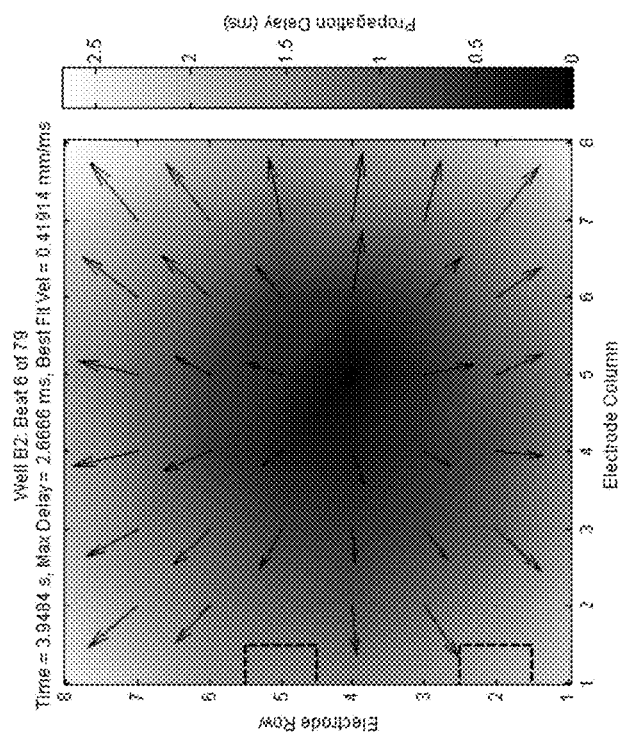
FIG. 7B is an exemplary map of a beat propagation pattern, depicting a beat that started in the center of a culture.

As shown in FIGS. 7A-B, these delay values can be graphically displayed to illustrate the beat propagation across the MEA 20. This allows for visualization of where each beat starts and ends as it travels across the array of electrodes 22 within a well of an MEA 20. The beat propagation pattern, and therefore the delay map, can vary from well to well of the MEA 20 and beat to beat. Sometimes the beat begins in the edge of the culture and propagates from one side to the other, as shown in FIG. 7A. At other times, a beat can originate in the center of the MEA and propagate outward, as in FIG. 7B.

Figure 8A:
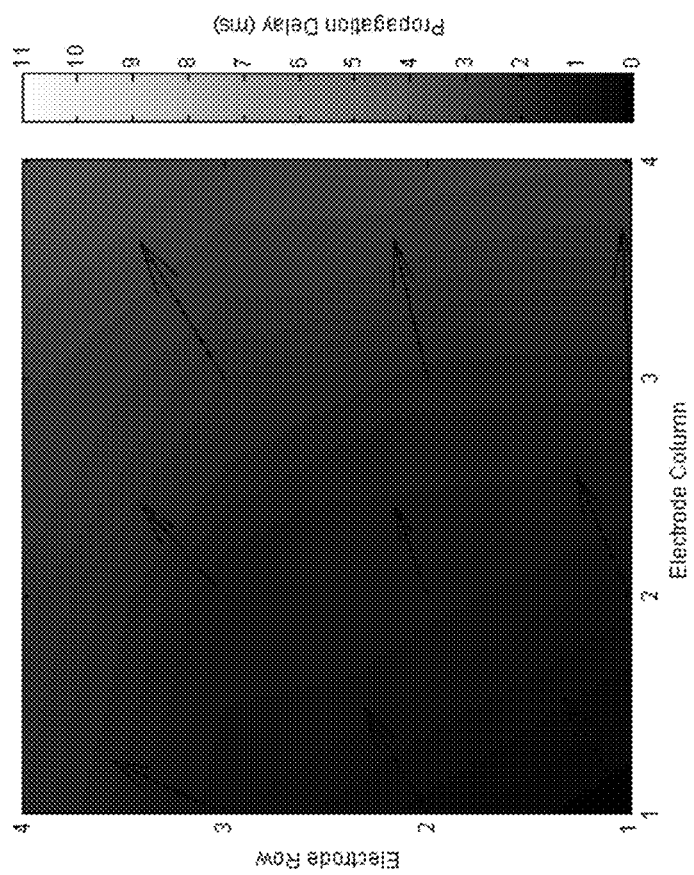
FIG. 8A is an exemplary map of a beat propagation pattern prior to addition of flecainide, a conduction blocker, to a cardiomyocyte culture.
Figure 8B:
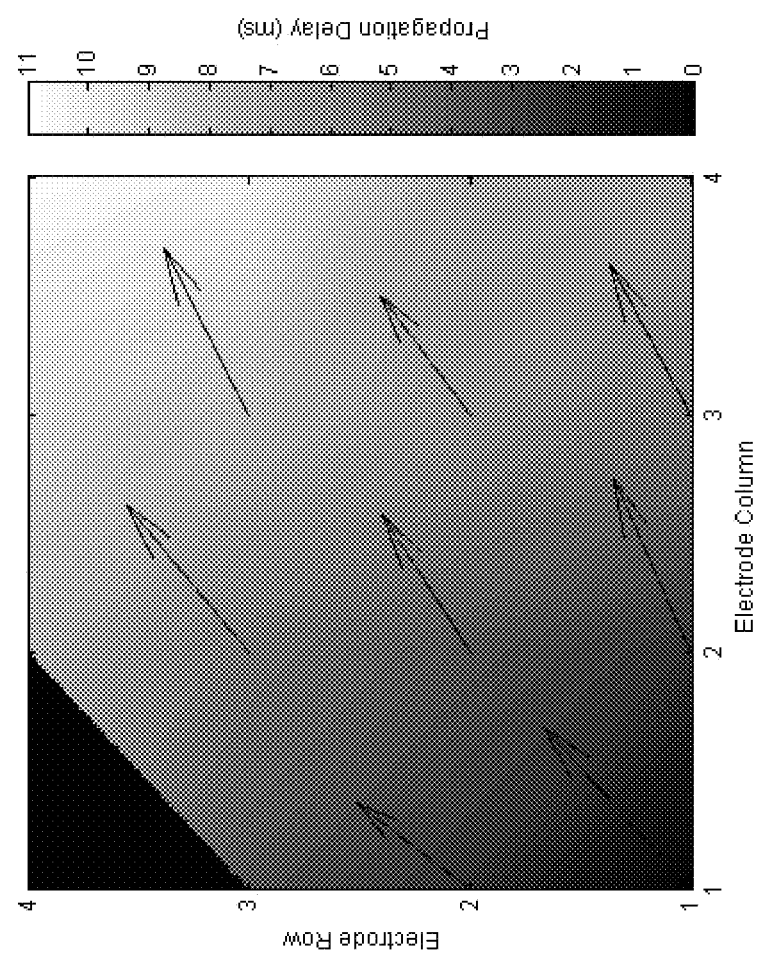
FIG. 8B is an exemplary map of a beat propagation pattern from the culture of FIG. 8A, after the introduction of flecainide.
Figure 8C:
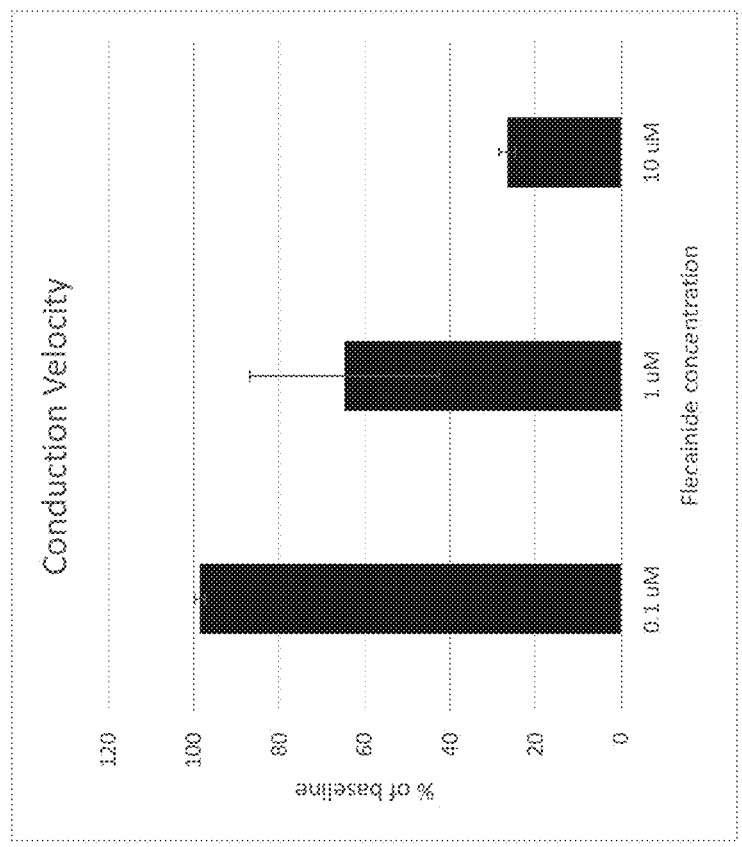
FIG. 8C is a bar graph of conduction velocities from an exemplary culture. In this example, conduction velocity slows with increasing concentrations of flecainide.

The GCV method can be useful for detecting changes induced by adding compounds to a cardiomyocyte culture. For example, flecainide is an exemplary compound known to slow beat conduction velocity by blocking sodium channels within the cardiomyocyte network. FIGS. 8A-B show maps of exemplary recordings made before (FIG. 8A) and after (FIG. 8B) the addition of flecainide to a cardiomyocyte culture. Measurements of the conduction velocity using the GCV method described above were systematically reduced as the concentration of flecainide was increased. FIG. 8C shows the exemplary GCV plotted as a function of the increasing flecainide concentration.

Cardiomyocyte cultures can be used to evaluate the safety risk of a candidate compound before the compound is advanced to human clinical trials. Growing cells on an MEA 20 allows baseline measurements of the field potential 7 to be made. These measurements can be used to assess parameters relating to the cellular health, function, and quality level of the culture. The parameters can include, for example, the amplitude 18 or maximum slope 8 of the depolarization spike, the beat period, the field potential duration 12, the global conduction velocity, or others. The measurements can then be repeated after the candidate compound has been exposed to the cellular network for a pre-determined amount of time. The degree to which any of the measurements changes upon addition of the candidate compound can inform the safety risk of the compound. These measurements can also be used to develop and characterize new stem cell lines, to compare the electrophysiology of cultured cardiomyocytes to in vivo cardiomyocytes, and/or to evaluate in vitro models of disease.

Disclosed herein are methods of filtering data obtained from electrically active cell cultures, such as cardiomyocyte cultures. The methods of filtering data can include gauging a quality level of the cell culture based on one or more parameters. The assessment of a cardiac cell culture may be more accurate if it is made using only cultures that are high quality, reliable, and healthy at baseline. Accuracy can be further improved by taking measurements across many individual beats. A threshold requirement can be defined that states 1) if a particular cardiomyocyte network should be included in an evaluation of the compound, and 2) which collection of individual beats should be used to make the measurements from that particular cardiomyocyte culture. Data and parameters determined from the data can be compared to the threshold requirement to determine if the data should be included in further analyses and/or scientific and characterization studies.

Parameters that can be used in the methods of filtering data and assessing a quality level of a culture can include but are not limited to: cell density, an ion channel distribution, arrhythmogenic behaviors, early after depolarization events, cell viability, number of pacemaker regions, distribution of pacemaker regions, pacemaker region activation frequency and timing, areas of conduction block, quality of attachment to a cell culture substrate, quality of contact with the electrodes, conduction velocity, global conduction velocity, field potential duration, repolarization morphology, amplitude of the field potential signal, slope of the field potential signal, beat period, variability in beat period, and beat propagation patterns of the electrically active cell culture based on the data collected.

Figure 9A:
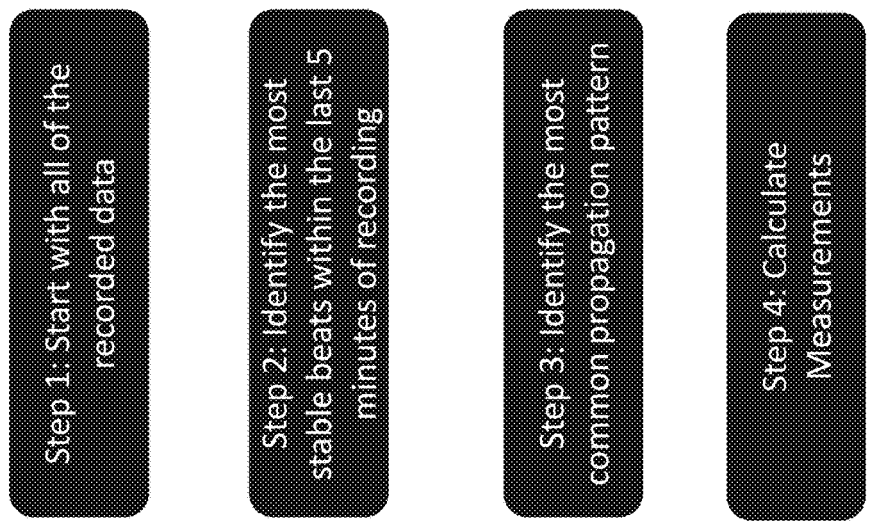
FIG. 9A is a flow chart of an exemplary method of filtering data.
Figure 9B:
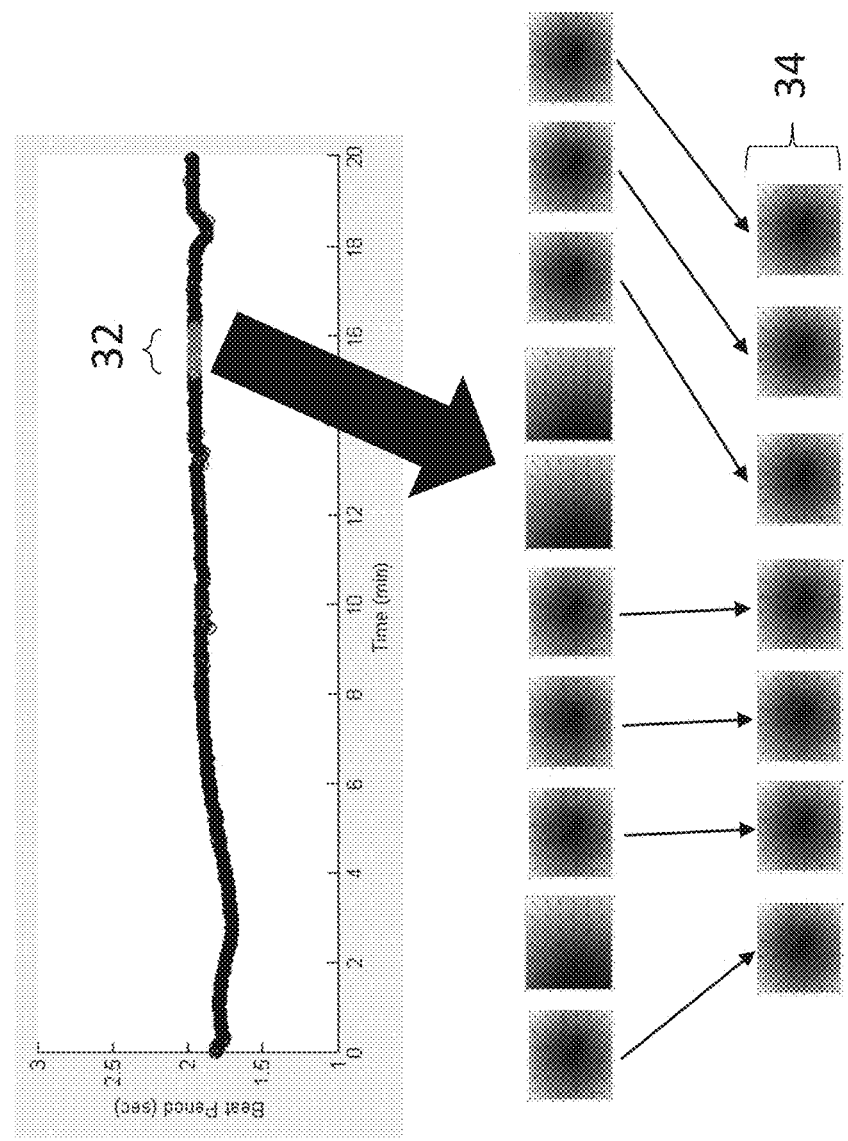
FIG. 9B shows a graph of an exemplary culture having a time window of temporal stability, and the corresponding beat propagation maps from that time window.

In one example of the method of filtering data, determining which wells and/or beats will be included in further scientific and characterization studies is a four-step process. A flow chart of the exemplary, four-step method of filtering data and assessing a quality level of a culture is shown in FIG. 9A. In the first step, data is recorded and prepared for processing. In a second step, a region of temporal stability is identified, as shown on the graph in FIG. 9B. A region of temporal stability 32 can be characterized as the timespan with the lowest coefficient of variation for a given parameter. The parameter can be, for example, the beat period. Alternatively, the parameter can be any parameter that varies over time. In a third step, beats that are spatially stable are identified within the selected timespan. Beats with spatial stability 34 follow the same propagation pattern, and can be identified using the beat propagation maps, as shown in FIG. 9B. These beats are selected for further analyses (the fourth step).

Methods of filtering data from inclusion in scientific and characterization studies can consider the spatial stability of one or more parameters. As described above, the timestamp of the beat detected by each electrode 22 can be used to generate a delay map illustrating the spatial pattern of beat propagation across a culture in a well of the MEA 20. In healthy cultures, the beat begins in one portion of the culture and propagates uniformly through the rest of the culture. This manifests in a delay map that indicates a single beat origin location and a smooth gradient of time delays through the rest of the array, as seen in FIG. 7B.

Figure 10A:
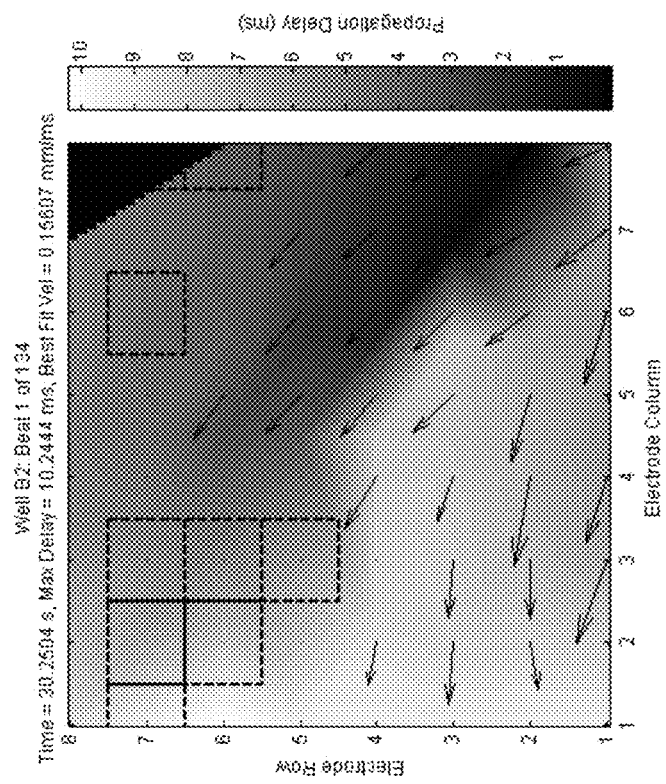
FIG. 10A shows a beat propagation map of an exemplary culture having a conduction block.
Figure 10B:
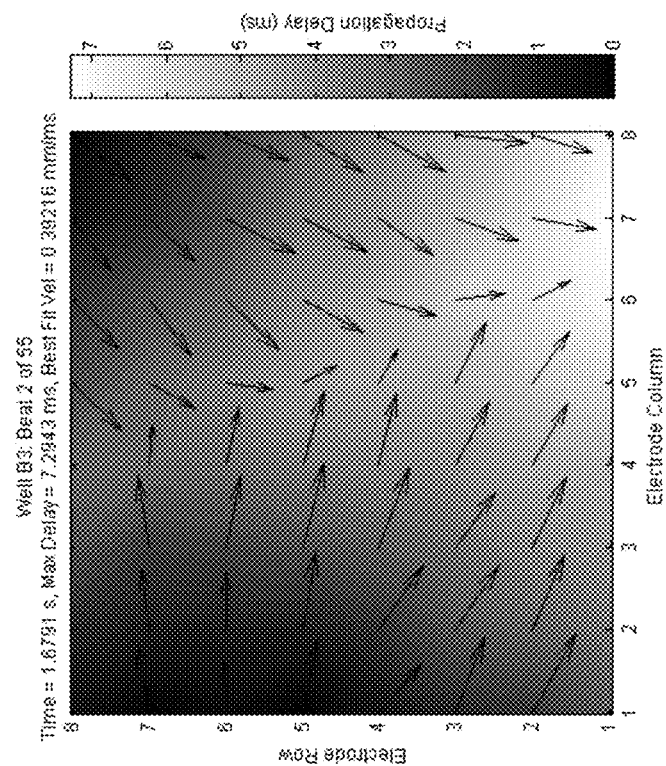
FIG. 10B shows a beat propagation map of an exemplary culture with multiple pacemaker regions.

Irregular propagation patterns, such as those seen in FIGS. 10A-B, may be due to morphological or functional causes. For example, a poor culture (due to low density, poor attachment, etc.) may result in beats not detected at all in large regions of the array. This results in gaps or holes in the propagation delay map. Alternatively, the cell culture may have a functional deficit affecting beat propagation. For example, impairments in the gap junctions may inhibit an action potential from one portion of the culture from travelling to neighboring cells. This results in propagation maps that may not be missing data points, but that indicate conduction block due to larger than expected delays as seen in FIG. 10A.

A culture can also have multiple pacemaker regions, resulting in action potentials propagating through the culture in two different directions simultaneously. This can result in a collision of the beats at particular regions of the culture, which manifests in the propagation delay maps as non-uniform beat propagation as seen in FIG. 10B. Exclusion of wells that have irregular propagation patterns at baseline can be helpful to scientific and characterization studies, especially if beat propagation and conduction velocity are relevant outcome metrics. In some implementations of the method, a threshold requirement can be set and compared to the assessment of spatial stability. If the spatial stability does not meet the threshold requirement, the data and/or particular culture can be excluded from further analyses, including scientific and characterization studies.

Figure 11:
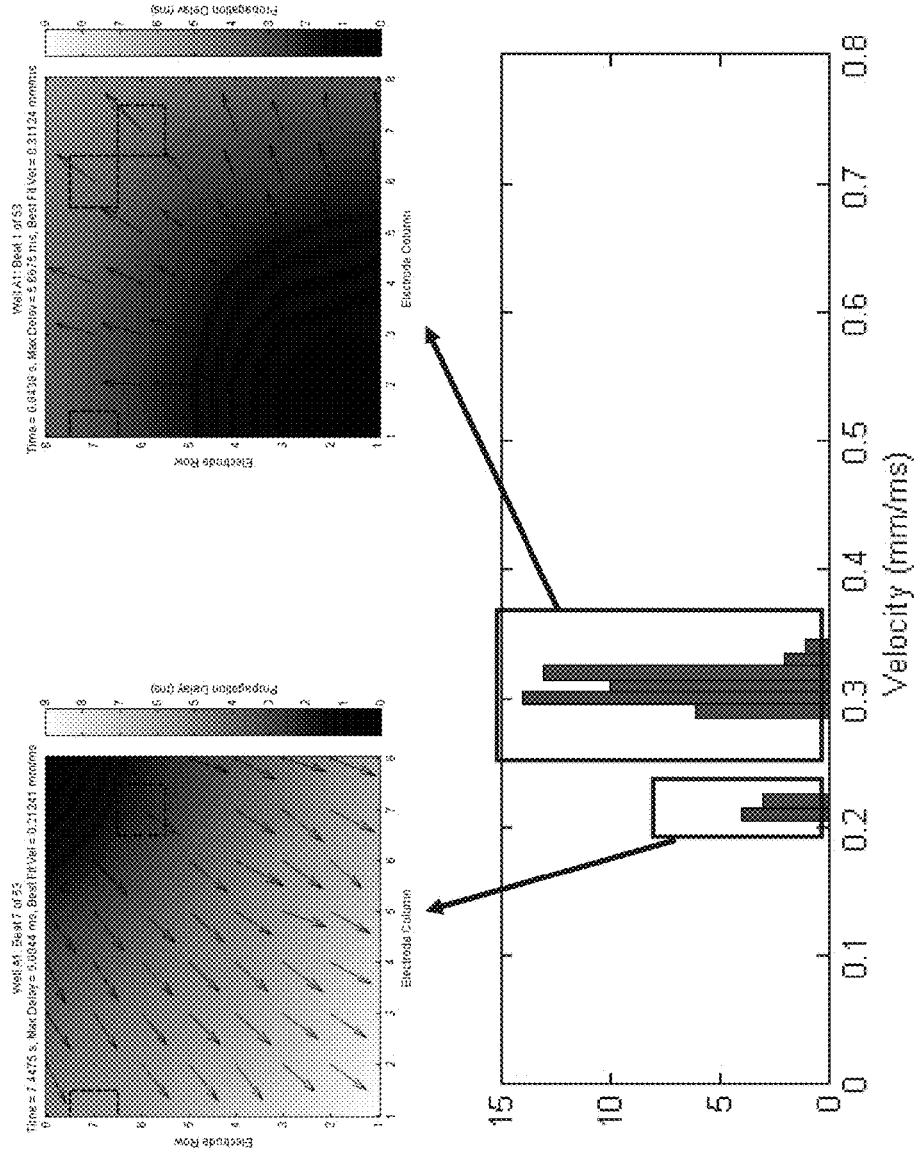
FIG. 11 shows two different beat propagation patterns originating from the same exemplary culture, and a histogram of conduction velocities from various beats within the same culture.

A single cardiomyocyte culture can present different propagation patterns at different times. This can be the result of, for example, changes in the syncytium as the culture develops over time, the existence of multiple pacemaking sites, or the addition of a compound affecting propagation. These varying propagation patterns can have different conduction velocities. An example of this phenomenon is shown in FIG. 11. As shown in FIG. 11, a beat originating in the upper right corner of the MEA and propagating downward and leftward can have a conduction velocity of, for example, 0.2 mm/ms. In contrast, a beat in the exact same well/culture originating in the lower left corner of the MEA and propagating upward and rightward can have a conduction velocity of, for example, 0.3 mm/ms. Including multiple propagation patterns in scientific studies can lead to noisy and potentially unreliable data. To account for spontaneous conduction variability, the propagation patterns can be sorted, and non-dominant patterns excluded from further analyses. This could produce a more reliable estimate of the conduction velocity and any changes caused by the experimental treatments.

Figure 12:
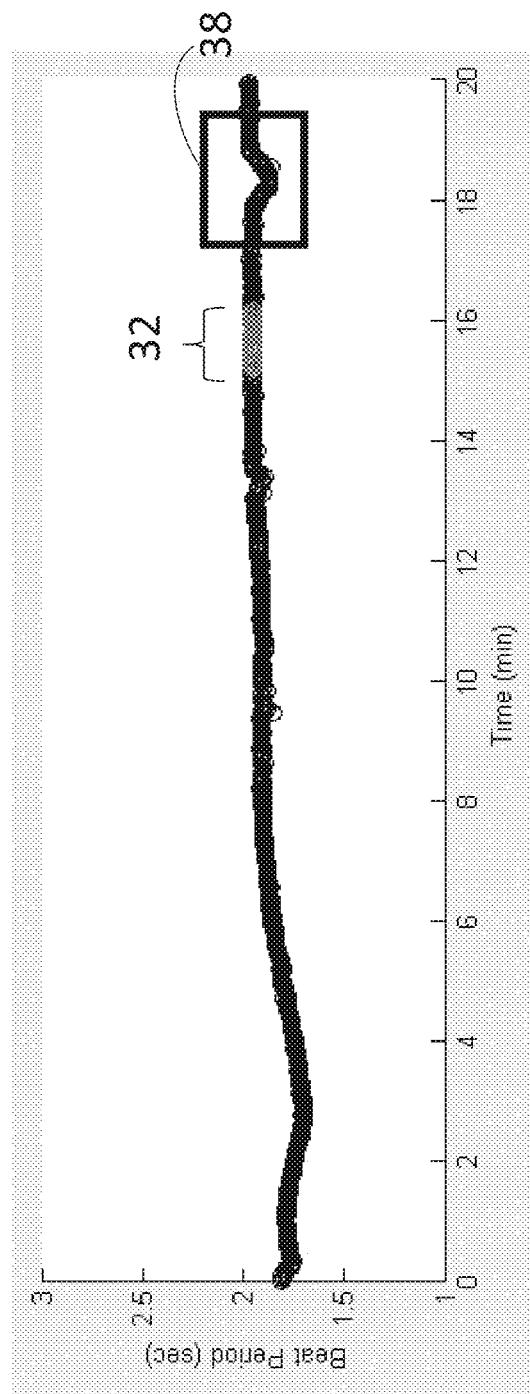
FIG. 12 shows a graph of data from an exemplary culture having temporal instability of the beat period.

Temporal stability of various parameters can also be considered when performing the methods of filtering data and gauging the quality level of an electrically active cell culture. For example, the beat period is the time difference between two consecutive beats. A healthy culture will exhibit low variability in beat period from beat to beat. However, spontaneous changes in beat period can occur. An example of this is shown in FIG. 12, which graphs the beat period over time and shows a region of spontaneous instability 38. The region of spontaneous instability 38 is the time frame in which the beat period dips down (around 18 minutes). The beat period then returns to the steady-state around 19 minutes. Incorporating measurements taken during this timeframe can lead a researcher to unreliable conclusions. Using measurements recorded during a timeframe with a stable beat period 32 can reduce noise and increase reliability. Other metrics, including but not limited to the field potential duration, are affected by modifications in the beat period. Therefore, it may be important to ensure the beat period has been stable for some time before analyzing the cardiac metrics. In some implementations of the method, a threshold requirement can be set and compared to an assessment of temporal stability. If the temporal stability does not meet the threshold requirement, the data and/or particular culture can be excluded from further analyses, including scientific and characterization studies.

In some implementations of the methods, a measure of stability, S, can be defined as the standard deviation of a parameter (for example, the beat period) over a collection of N beats $\psi$. A lower value of S indicates greater stability, given by the following equation:

$$S(\psi) = \sqrt{\frac{1}{N}\sum_{i=1}^{N}(\psi_i - \bar{\psi})^2} \text{ where } \bar{\psi} = \frac{1}{N}\sum_{i=1}^{N}\psi_i$$

The most stable set of N beats, $\psi_{stable}$, is chosen by minimizing the stability metric S:

$$\psi_{stable} = \operatorname*{argmin}_{\psi} S(\psi)$$

If the beat periods are unstable throughout the entire measurement period for a baseline condition, the well can be excluded from further participation in the study.

An unhealthy, low quality culture, or a culture that has been exposed to a dangerous compound, may exhibit irregular beating. Irregular beat periods induced by addition of a compound may be an indication of the compound being pro-arrhythmic, which is an important determination in cardiac drug safety testing. Arrhythmias can present in different forms within the culture, but in all cases a measurement of the temporal stability over a collection of beats, as described above, can be used to detect the arrhythmic activity.

Figure 13:
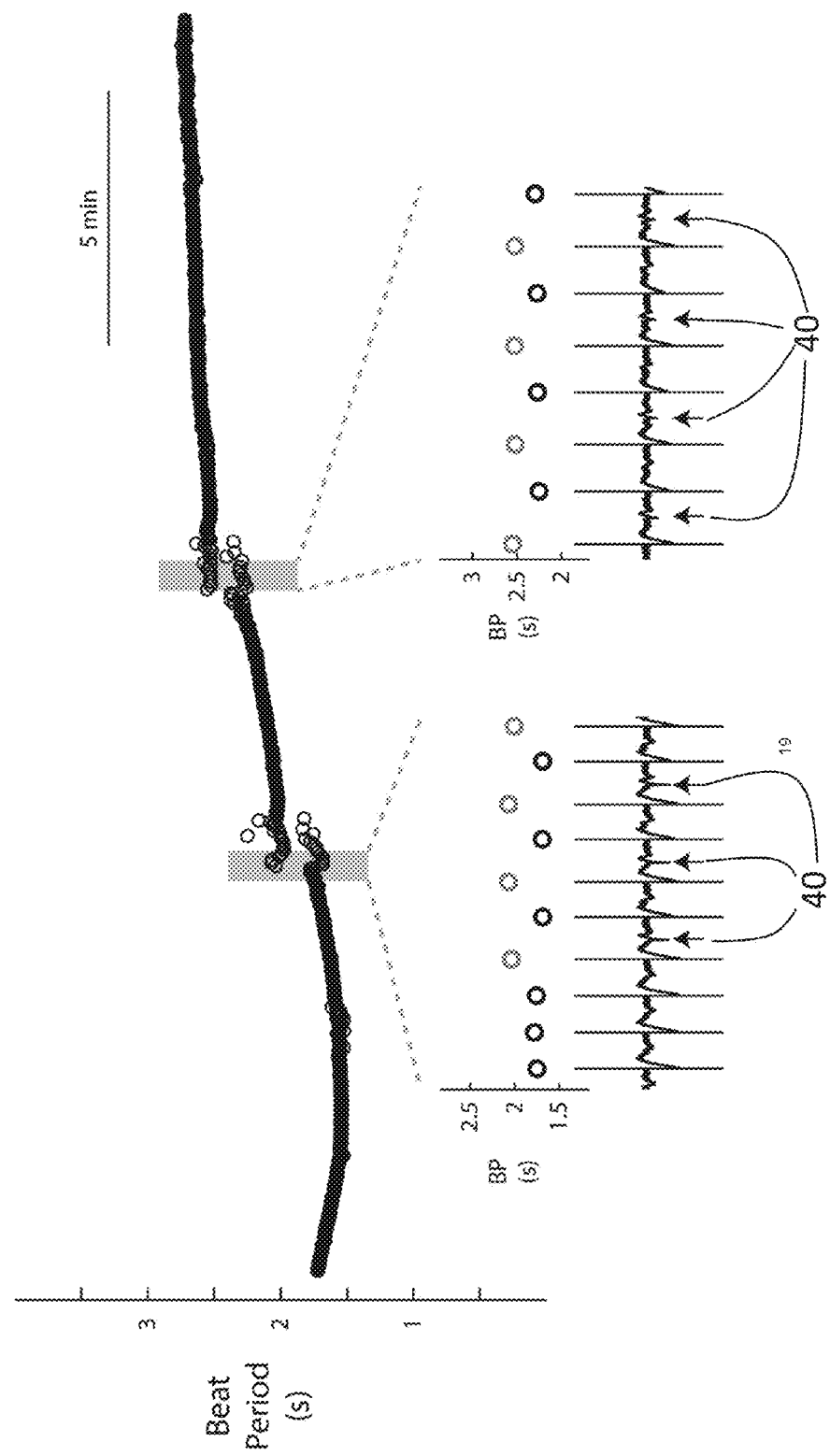
FIG. 13 shows a graph of an exemplary culture having temporal instability of the beat period. In various regions, the field potential signals are shown to demonstrate the presence of early afterdepolarization events corresponding to regions of temporal instability.

A specific arrhythmic pattern can further indicate the presence of an early afterdepolarization (EAD) event, which is another important pro-arrhythmic indicator. Other pro-arrhythmic indicators can include ectopic beats, triggered activity, "rolling" EADs, or repolarization instability. For example, as shown in FIG. 20, pro-arrhythmic indicators (EAD 2002, rolling EAD 2004, and ectopic beat 2006) are shown in comparison to normal beating 2000. Detection of EADs can assist researchers in determining the safety of a candidate pharmaceutical compound. An EAD is an abnormal depolarization event which occurs during the plateau phase 4 of the cardiac action potential 1, before repolarization is complete. This manifests as a small depolarization event 40 in the field potential around the time that repolarization (t-wave) 10 is expected, as seen in FIG. 13.

Detection of EADs can be automated by detecting regions of beat period "bi-stability" within the time frame of measurement. A period of "bi-stability" is characterized by a rapid switching of the beat period between two different values, as is illustrated in FIG. 13. The two beat period values can be defined as SHORT and LONG, where the SHORT beat period is less than the value of the LONG beat period. Within a bi-stable region, the LONG beat period is highly predictive of the presence of an EAD 40. This is illustrated in FIG. 13 where each of the LONG beat periods exhibits an EAD feature 40. The switching between the SHORT and LONG beat period may, or may not, occur on each consecutive beat. Thus a measure of the proportion of LONG beats to SHORT beats can be used as a measure of the intensity of the arrhythmia, or arrhythmic load. Alternatively or additionally, the LONG beats and/or the SHORT beats can be used to determine a quantitative measure of cardiac beating including, but not limited to, beat period, field potential duration (FPD), depolarization spike amplitude, or conduction velocity.

Figure 14A:
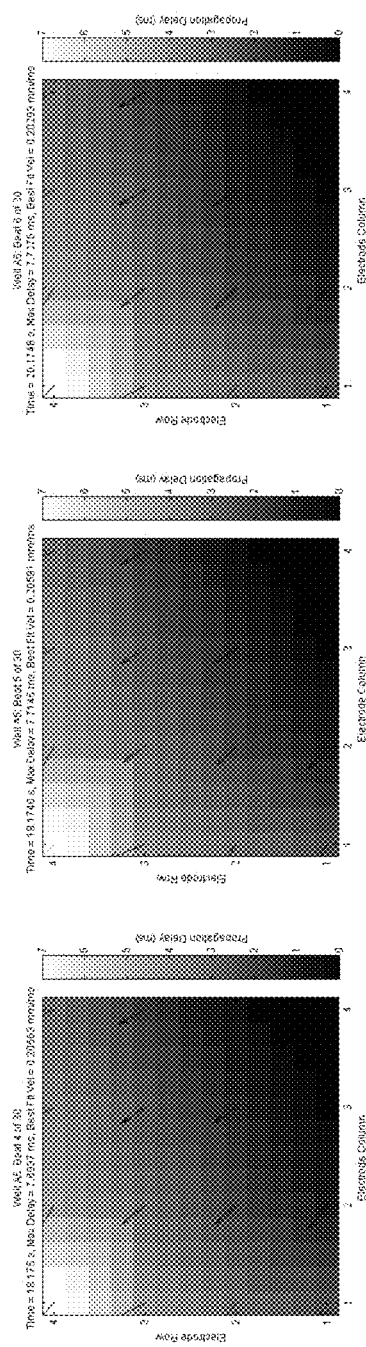
FIG. 14A shows beat propagation maps of an exemplary culture being paced from the lower right hand corner.
Figure 14B:
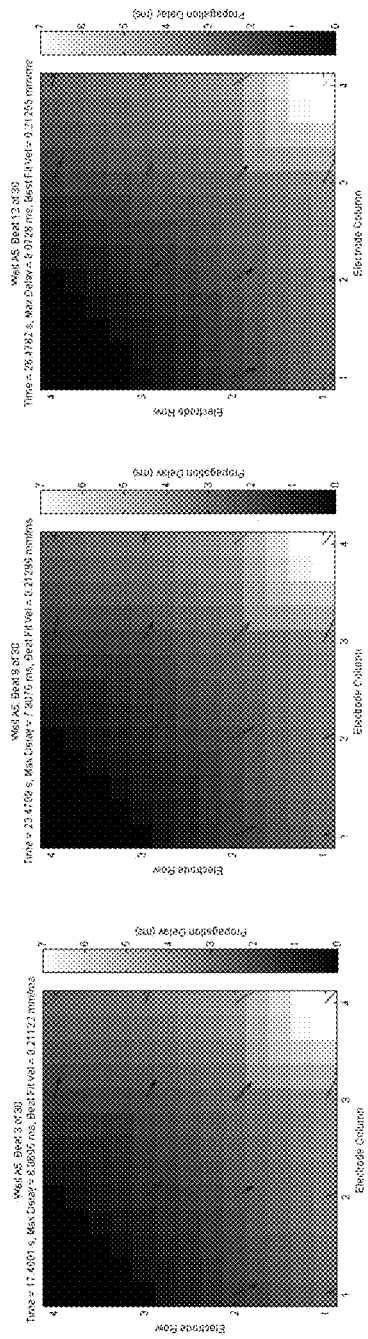
FIG. 14B shows beat propagation maps of an exemplary culture being paced from the upper left hand corner.
Figure 15:
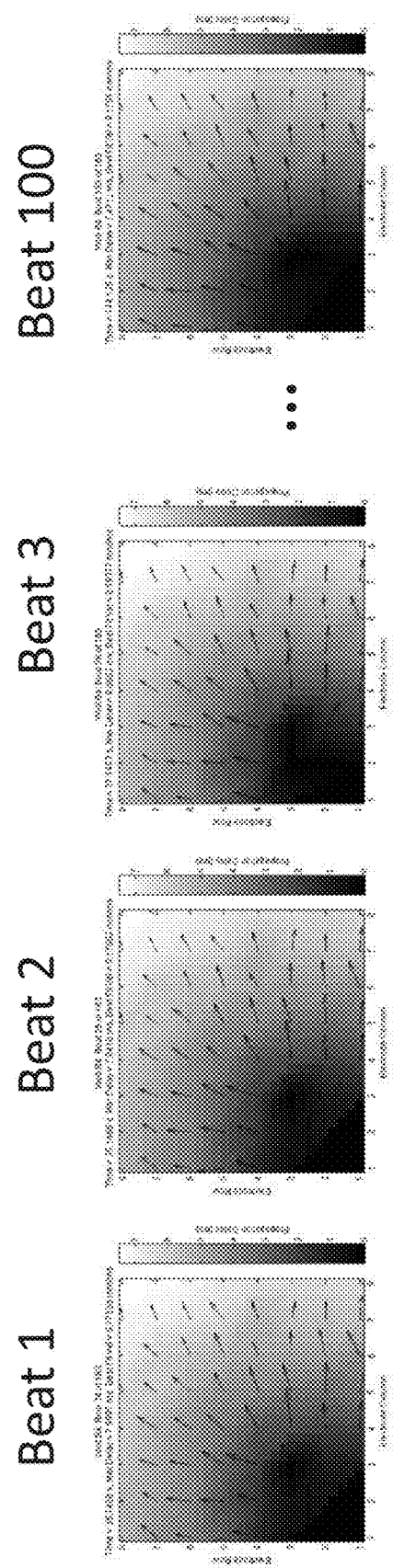
FIG. 15 shows beat propagation maps of an exemplary culture being paced from the lower left hand corner.
Figure 16:
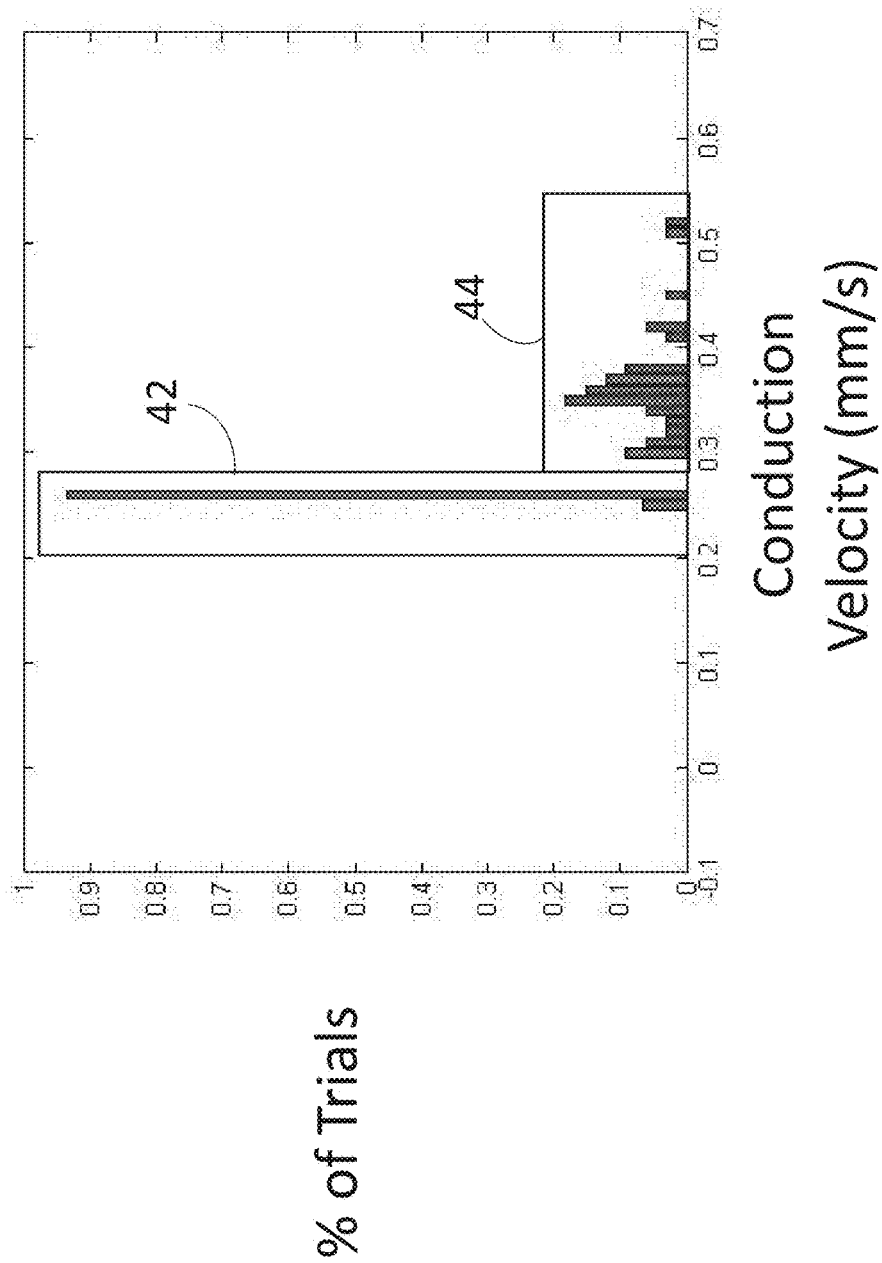
FIG. 16 shows a histogram of the conduction velocity from a single exemplary well under paced versus spontaneous conditions.

Temporal and spatial stability can be altered, and in some cases improved, by electrically pacing or electrically stimulating the culture. To pace a cardiomyocyte culture plated on an MEA 20, electrical current is applied to the culture via one or more of the microelectrodes 22. This current triggers a well-wide beat in the culture. Electrical stimulation can be applied at 1 Hz, for example, so that the culture beats reliably at 1 Hz. As seen in FIGS. 14A-B, pacing causes the beat to reliably begin in the region being stimulated. The beat propagates outward from there. In FIG. 14A, the cardiomyocyte culture is first stimulated in the lower right corner of the well, causing beats to initiate from the lower right. In FIG. 14B, the culture is stimulated in the upper left corner of the well, causing the beats to initiate from the upper left. Pacing reduces the variability of many parameters, including but not limited to the beat propagation pattern and the conduction velocity. The spatial stability of the beat propagation pattern is illustrated by FIG. 15, where the propagation pattern does not change across the paced beats. FIG. 16 shows a histogram of the conduction velocity over time, comparing the frequency that a beat propagates at a given velocity. The improvement in the temporal stability upon pacing is evident by the increased number of beats having the same conduction velocity for the paced group 42 as compared to the spontaneous group 44. Alternatively or additionally, to pace a cardiomyocyte culture plated on an MEA 20, optical stimulation can be delivered to the culture via one or more light emitting elements sets. As described herein, a light emitting element set can be provided corresponding to each of the plurality of culture wells 114. Alternatively or additionally, to pace a cardiomyocyte culture plated on an MEA 20, the temperature of the culture can be adjusted, for example, using heating and/or cooling elements associated with each of the plurality of culture wells 114.

As will be appreciated by one skilled in the art, at least portions of the methods and systems can take the form of a computer program product on a computer-readable storage medium having computer-readable program instructions (e.g., computer software) embodied in the storage medium. Any suitable computer-readable storage medium can be utilized including hard disks, CD-ROMs, optical storage devices, or magnetic storage devices.

These computer program instructions can also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions can also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Figure 17:
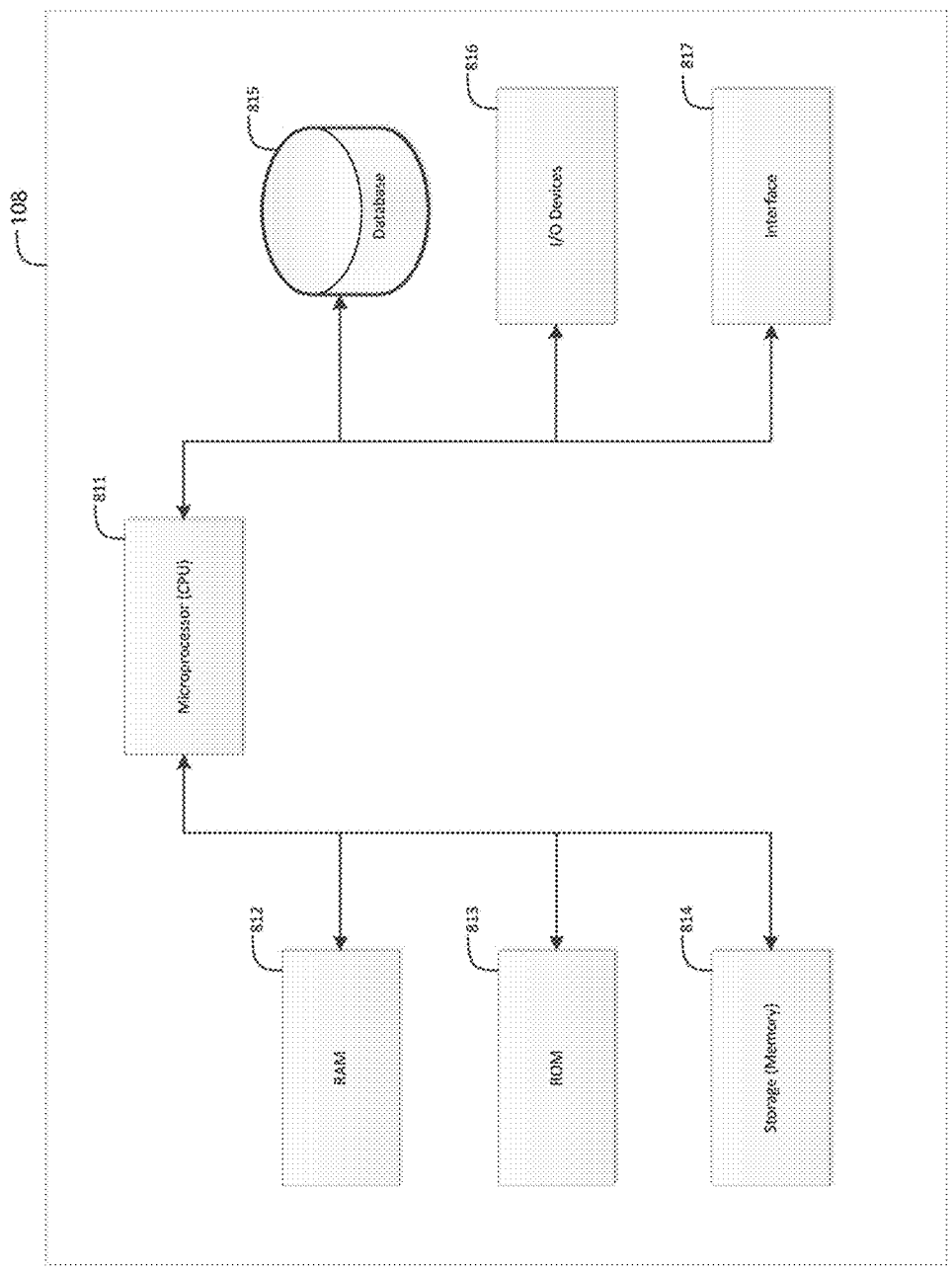
FIG. 17 is an exemplary schematic diagram of the electronics that are adapted to interface with a MEA.

FIG. 17 illustrates an exemplary schematic diagram associated with electronics 108 that is adapted to interface with a multiwell microelectrode array (MEA) 20, which can be used in the systems and methods described herein. Electronics 108 can include a processor-based device that includes its own microcontroller, volatile and non-volatile memory, one or more databases, and one or more interfaces for communicating data with a user.

As described above, arrhythmia analysis according to conventional techniques consists of identifying, in a binary sense, whether an arrhythmic event has or has not occurred during a defined analysis time window. Additionally, recent studies (e.g., Guo, L. et al. and Gilchrist, K. H. et al.) have aimed to provide an analog, or graded, quantification of the arrhythmia burden induced by a test compound. However, these recent studies have not involved assigning quantitative arrhythmic risk scores based on a relationship between beat period (or beat rate) associated with an electroactive cell culture and arrhythmic indicators or events. As described below, beat period (or beat rate, which is the inverse of beat period) can be adjusted or controlled by pacing the electroactive cell culture, and pro-arrhythmic indicators can be automatically identified and counted at each of a plurality of beat periods. Additionally, a quantitative measure of arrhythmia burden can be assigned based on the relationship between beat period and pro-arrhythmic indicators.

Figure 18:
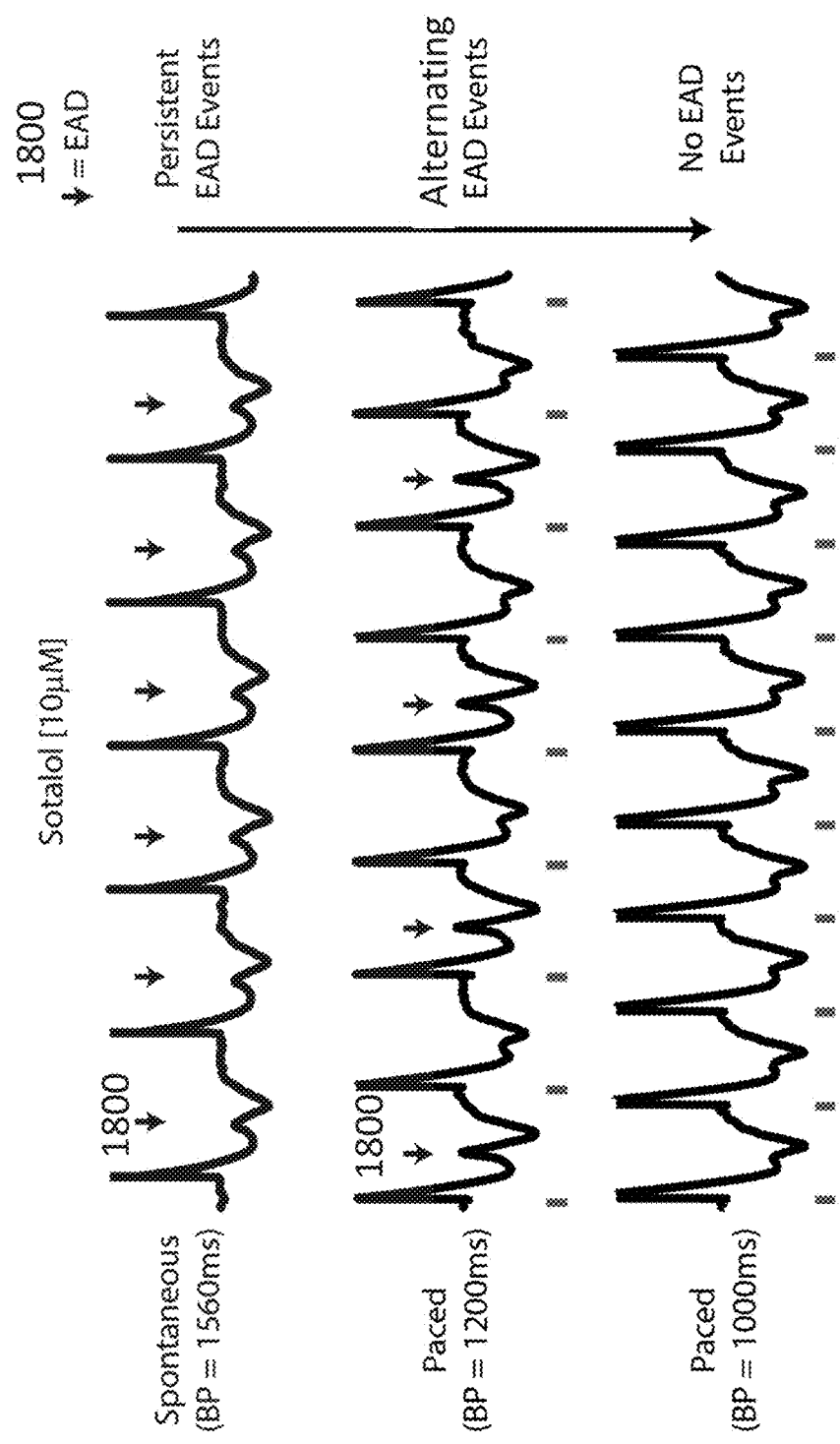
FIG. 18 illustrates the rate-dependence of early afterdepolarization (EAD) events.

Referring now to FIG. 18, the rate-dependence of early afterdepolarization (EAD) events is shown. Sotalol, an example pro-arrhythmic compound, was contacted with an electrically active cell culture (e.g., cardiomyocytes) and induced persistent arrhythmic activity at the spontaneous beat period of 1560 ms, with EADs 1800 (shown by arrows in FIG. 18) occurring during each beat. The arrhythmic burden is defined as a 100% at the spontaneous beat period, i.e., pro-arrhythmic indicators occurring during each beat. The beat-by-beat prevalence of arrhythmic indicators, such as EAD events, can be assessed by determining the percentage (or ratio) of beats that exhibit arrhythmic indicators from an overall number of beats. The overall number of beats can be the number of beats in a time period of analysis having any length. The percentage of beats exhibiting pro-arrhythmic indicators can be referred to as the arrhythmia burden. As shown in FIG. 18, the arrhythmia burden is dependent on the beating rate of the electrically active cell culture. As the beating rate increases (i.e., the beat period decreases) through pacing, the arrhythmia burden is reduced (e.g., arrhythmia burden of 50% at beat period of 1200 ms), and then eventually reduced to arrhythmia burden of 0% at the 1 Hz pacing rate (or beat period of 1000 ms). It should be understood that sotalol is only provided as an example compound or drug and that other compounds or drugs can be placed in contact with the electrically active cell culture. Additionally, this disclosure contemplates that the techniques described herein are applicable with other compounds or drugs.

Figure 19:
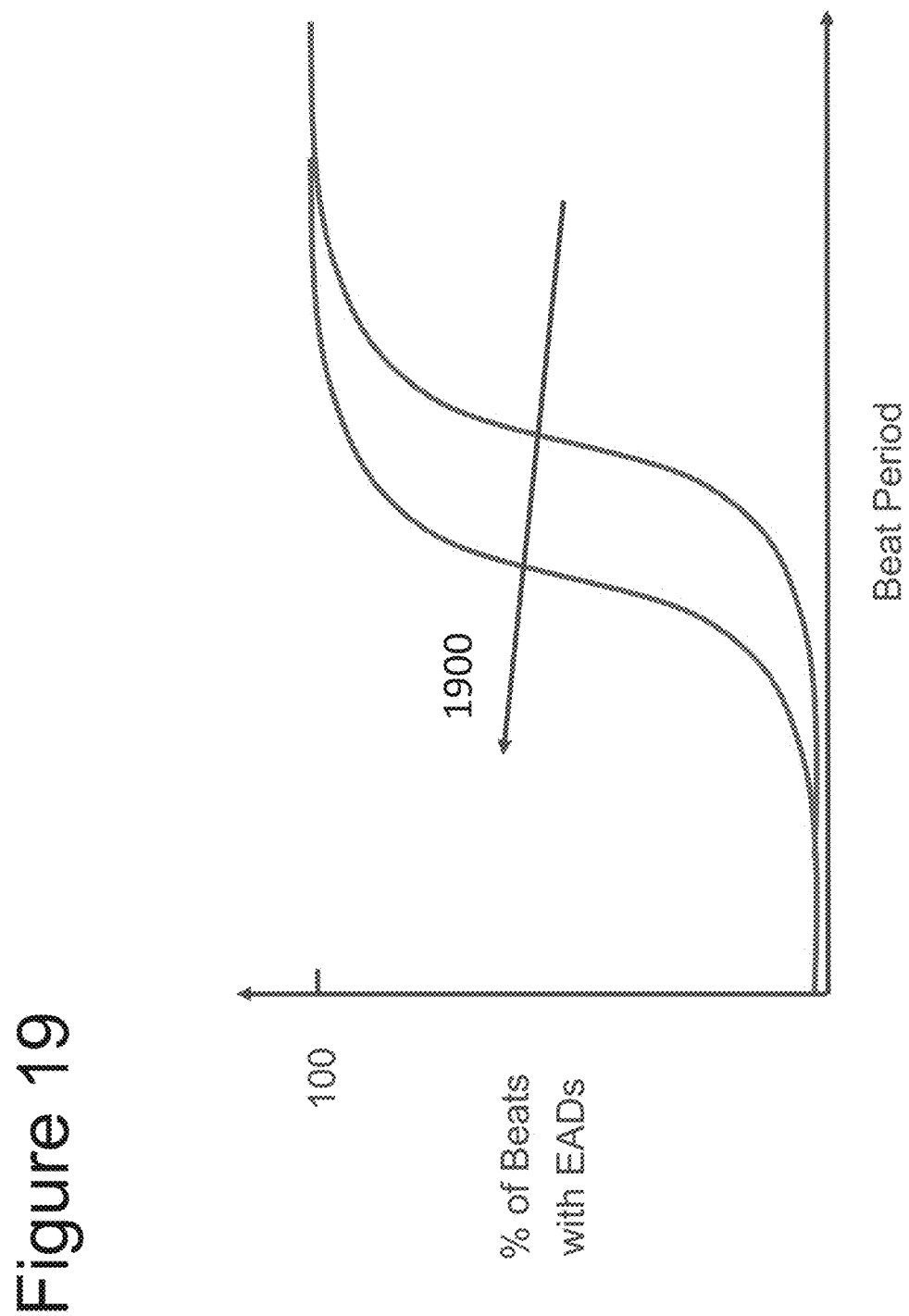
FIG. 19 is a curve illustrating the relationship between beat period and arrhythmic burden.

According to implementations described herein, the relationship between beating rate and arrhythmia burden can be measured and analyzed. Additionally, by pacing the activity of the electrically active cell culture at a plurality of frequencies following drug or compound addition, the arrhythmia burden can be determined at each of the plurality of frequencies. The relationship between beat period and arrhythmia burden can then be plotted as shown in FIG. 19. The difference between two curves, shown by arrow 1900 in FIG. 19, can be used to inform arrhythmia risk. For example, in FIG. 19, the curve on the left may be considered a higher arrhythmia risk. Additionally, a quantitative measure of the arrhythmia burden can be obtained from the relationship between beat period and arrhythmia burden. For example, the quantitative measure of arrhythmia burden can be a specific beat period (or beat rate) associated with the electrically active cell culture at which a predetermined percentage (e.g., 50%) of beats exhibit the pro-arrhythmic indicator (e.g., EAD event). EAD50 can be defined as the specific beat period (or beat rate) that produces an EAD on 50% of the beats, or 50% arrhythmia burden. This quantitative measure provides a means for comparing the pro-arrhythmic risk of different concentrations of the same drug and across different drugs. The quantitative measure can be used to assess the safety of a compound or drug, for example, the quantitative measure can be used to estimate, evaluate, or rank the safety of a compound or drug. It should be understood that EAD50 is provided only as one example. The arrhythmic burden can have other values. For example, EAD20 can be similarly defined as the beat period (or beat rate) that produces a pro-arrhythmic indicator such as an EAD on 20% of the beats.

Alternatively or additionally, the quantitative measure of arrhythmia burden can be obtained from the curve defining the relationship between beat period and arrhythmic burden (e.g., FIG. 19). For example, the quantitative measure can include, but is not limited to, a slope of a portion of the curve defining the relationship between beat period and arrhythmic burden. Alternatively, the quantitative measure can be a maximum amplitude (e.g., the maximum EAD percentage) of the curve defining the relationship between beat period and arrhythmic burden. Arrhythmia burden can also be quantified by pacing the electrically active culture at a fixed beat rate (e.g., 1 Hz) and identifying the concentration at which a compound or drug induces a predetermined percentage of beats exhibiting the pro-arrhythmic indicator. For example, the electrically active culture can be paced at a fixed beat rate of 1 Hz, and the concentration of the compound or drug can be adjusted to achieve EAD50. This concentration can be referred to as the EAD50 concentration. As described above, the quantitative measure provides a means for comparing the pro-arrhythmic risk of different concentrations of the same drug and across drugs. It should be understood that the fixed beat rate of 1 Hz and EAD50 are provided only as examples and can have other values.

According to one embodiment, electronics 108 can include one or more hardware components such as a central processing unit (CPU) or microprocessor 811, a random access memory (RAM) module 812, a read-only memory (ROM) module 813, a memory or data storage module 814, a database 815, one or more input/output (I/O) devices 816, and an interface 817. Alternatively and/or additionally, electronics 108 can include one or more software media components such as a computer-readable medium including computer-executable instructions for performing methods consistent with certain disclosed embodiments. It is contemplated that one or more of the hardware components listed above can be implemented using software. For example, storage 814 can include a software partition associated with one or more other hardware components of control and monitoring system 800. Electronics 108 can include additional, fewer, and/or different components than those listed above. It is understood that the components listed above are exemplary only and not intended to be limiting.

CPU 811 can include one or more processors, each configured to execute instructions and process data to perform one or more functions associated with electronics 108. As illustrated in FIG. 8, CPU 811 can be communicatively coupled to RAM 812, ROM 813, storage 814, database 815, I/O devices 816, and interface 817. CPU 811 can be configured to execute sequences of computer program instructions to perform various processes. The computer program instructions can be loaded into RAM 812 for execution by CPU 811.

RAM 812 and ROM 813 can each include one or more devices for storing information associated with an operation of electronics 108 and/or CPU 811. For example, ROM 813 can include a memory device configured to access and store information associated with control and monitoring system 800, including, for example, stimulation schemes for different types of experiments. RAM 812 can include a memory device for storing data associated with one or more operations of CPU 811. For example, ROM 303 can load instructions into RAM 302 for execution by CPU 811.

Storage 814 can include any type of mass storage device configured to store information that CPU 811 can need to perform processes consistent with the disclosed embodiments. For example, storage 814 can include one or more magnetic and/or optical disk devices, such as hard drives, CD-ROMs, DVD-ROMs, or any other type of mass media device. Alternatively or additionally, storage 814 can include flash memory mass media storage or other semiconductor-based storage medium. Database 815 can include one or more software and/or hardware components that cooperate to store, organize, sort, filter, and/or arrange data used by electronics 108 and/or CPU 811.

I/O devices 816 can include one or more components configured to communicate information with a component or user associated with electronics 108. For example, I/O devices 816 can include a console with an integrated keyboard and mouse to allow a user to input parameters associated with electronics 108. I/O devices 816 can also include a display including a graphical user interface (GUI) for providing a network management console for network administrators to configure electronics 108. I/O devices 816 can also include peripheral devices such as a printer for printing information associated with electronics 108, a user-accessible disk drive (e.g., a USB port, a floppy, CD-ROM, or DVD-ROM drive, etc.) to allow a user to input data stored on a portable media device, a microphone, a speaker system, or any other suitable type of interface device. I/O devices can be configured to output network analysis results and traffic characteristics.

Interface 817 can include one or more components configured to transmit and receive data via a communication network, such as the Internet, a local area network, a workstation peer-to-peer network, a direct link network, a wireless network, MEA 20, or any other suitable communication platform. For example, interface 817 can include one or more modulators, demodulators, multiplexers, demultiplexers, network communication devices, wireless devices, antennas, modems, and any other type of device configured to enable data communication via a communication network. According to one embodiment, interface 817 can be coupled to or include wireless communication devices, such as a module or modules configured to transmit information wirelessly using Wi-Fi or Bluetooth wireless protocols.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It should be appreciated that the logical operations described herein with respect to the various figures may be implemented (1) as a sequence of computer implemented acts or program modules (i.e., software) running on a computing device (e.g., the computing device described in FIG. 17), (2) as interconnected machine logic circuits or circuit modules (i.e., hardware) within the computing device and/or (3) a combination of software and hardware of the computing device. Optionally, the logical operations described herein with respect to the various figures can be implemented using the high-throughput electrophysiology culture system including a microelectrode array (MEA) as described in FIG. 1. It should be understood that the logical operations described herein with respect to the various figures can be implemented using other electrophysiology culture systems (i.e., not limited to systems having an MEA). Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 21:
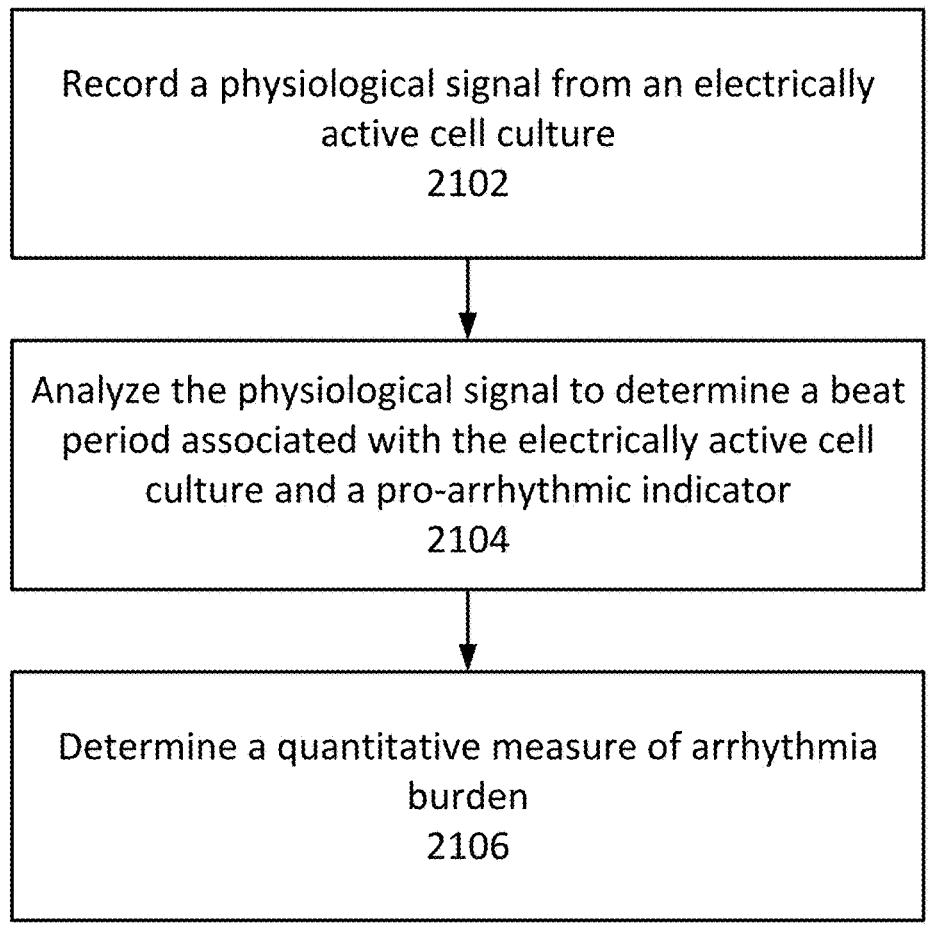
FIG. 21 is a flow diagram illustrating example operations for quantifying an arrhythmia burden.

Referring now to FIG. 21, example operations for quantifying an arrhythmia burden are shown. At 2102, a physiological signal from an electrically active cell culture is recorded. As described herein, the physiological signal can be recorded using a sensor such as one or more electrodes, photosensors, etc. In some implementations, the physiological signal can be recorded using an MEA, e.g., the MEA of the high-throughput electrophysiology culture system 100 of FIG. 1. The physiological signal can be transmitted to electronics (e.g., a computing device) communicatively coupled with the sensor. In addition, the physiological signal can be a cardiac beat signal. The cardiac beat signal can include at least one of a field potential signal, an impedance signal, an action potential signal, a calcium signal, an optical signal, or combinations thereof. At 2104, the physiological signal is analyzed to determine a beat period (or beat rate) associated with the electrically active cell culture and a pro-arrhythmic indicator. Optionally, one or more pro-arrhythmic indicators can be identified automatically (e.g., as described in FIG. 22). As described herein, the beat period can be the time interval from one depolarization to the next of the physiological signal, for example. At 2106, a quantitative measure of arrhythmia burden is determined.

As described herein, the quantitative measure of arrhythmia burden can be a relationship between the beat period associated with the electrically active cell culture and the pro-arrhythmic indicator. For example, the quantitative measure of arrhythmia burden can be a measure of beats exhibiting a pro-arrhythmic indicator (or other arrhythmic indicator). For example, the quantitative measure of arrhythmia burden can be a specific beat period (or beat rate) associated with the electrically active cell culture at which a predetermined percentage of beats exhibit the pro-arrhythmic indicator such as EAD 50 or EAD 20. Alternatively or additionally, the quantitative measure of arrhythmia burden can be based on a curve that defines the relationship between the beat period associated with the electrically active cell culture and the percentage of beats exhibiting the pro-arrhythmic indicator (e.g., FIG. 19). As described herein, the electrically active cell culture can be paced using electrical, optical, and/or temperature stimulation to generate the curve. Alternatively or additionally, the quantitative measure of arrhythmia burden can be based on a number of beats classified as having a long beat period. The quantitative measure provides a means for comparing the pro-arrhythmic risk of different concentrations of the same drug and across different drugs. Thus, the quantitative measure can be used to assess the safety of a compound or drug, for example, the quantitative measure can be used to estimate, evaluate, or rank the safety of a compound or drug.

Figure 22:
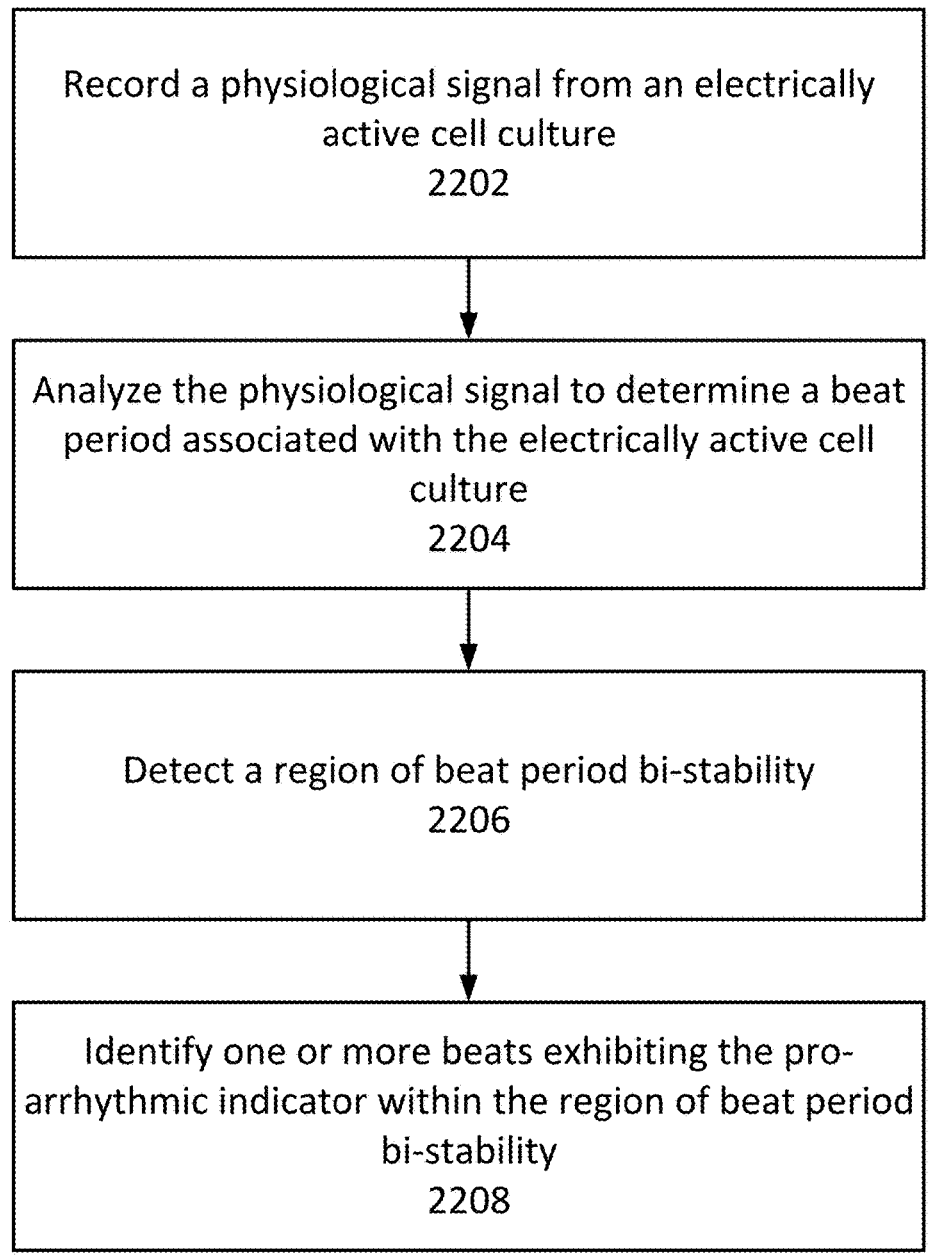
FIG. 22 is a flow diagram illustrating example operations for identifying one or more beats exhibiting a pro-arrhythmic indicator.

Referring now to FIG. 22, example operations for identifying one or more beats exhibiting a pro-arrhythmic indicator are shown. Optionally, the example operations of FIG. 22 can be used to automatically identify one or more beats exhibiting a pro-arrhythmic indicator. At 2202, a physiological signal from an electrically active cell culture is recorded. As described herein, the physiological signal can be recorded using a sensor such as one or more electrodes, photosensors, etc. In some implementations, the physiological signal can be recorded using an MEA, e.g., the MEA of the high-throughput electrophysiology culture system 100 of FIG. 1. The physiological signal can be transmitted to electronics (e.g., a computing device) communicatively coupled with the sensor. In addition, the physiological signal can be a cardiac beat signal. The cardiac beat signal can include at least one of a field potential signal, an impedance signal, an action potential signal, a calcium signal, an optical signal, or combinations thereof. At 2204, the physiological signal is analyzed to determine a beat period associated with the electrically active cell culture. As described herein, the beat period can be the time interval from one depolarization to the next of the physiological signal, for example. At 2206, a region of beat period bi-stability is detected. An example region of beat period bi-stability is illustrated by FIG. 13, where beat period rapidly switches between LONG and SHORT beat periods. At 2208, the one or more beats exhibiting the pro-arrhythmic indicator are identified within the region of beat period bi-stability. For example, as described herein, the LONG beat period can be highly predictive of the presence of an EAD. Optionally, a quantitative measure of arrhythmic burden can be determined based on the number of beats exhibiting the pro-arrhythmic indicator as described herein. Optionally, a quantitative measure of cardiac beating can be determined based on the beats having the LONG beat period and/or the SHORT beat period. Optionally, the quantitative metric can be used to assess the safety of a pharmaceutical compound as described herein.

Figure 23:
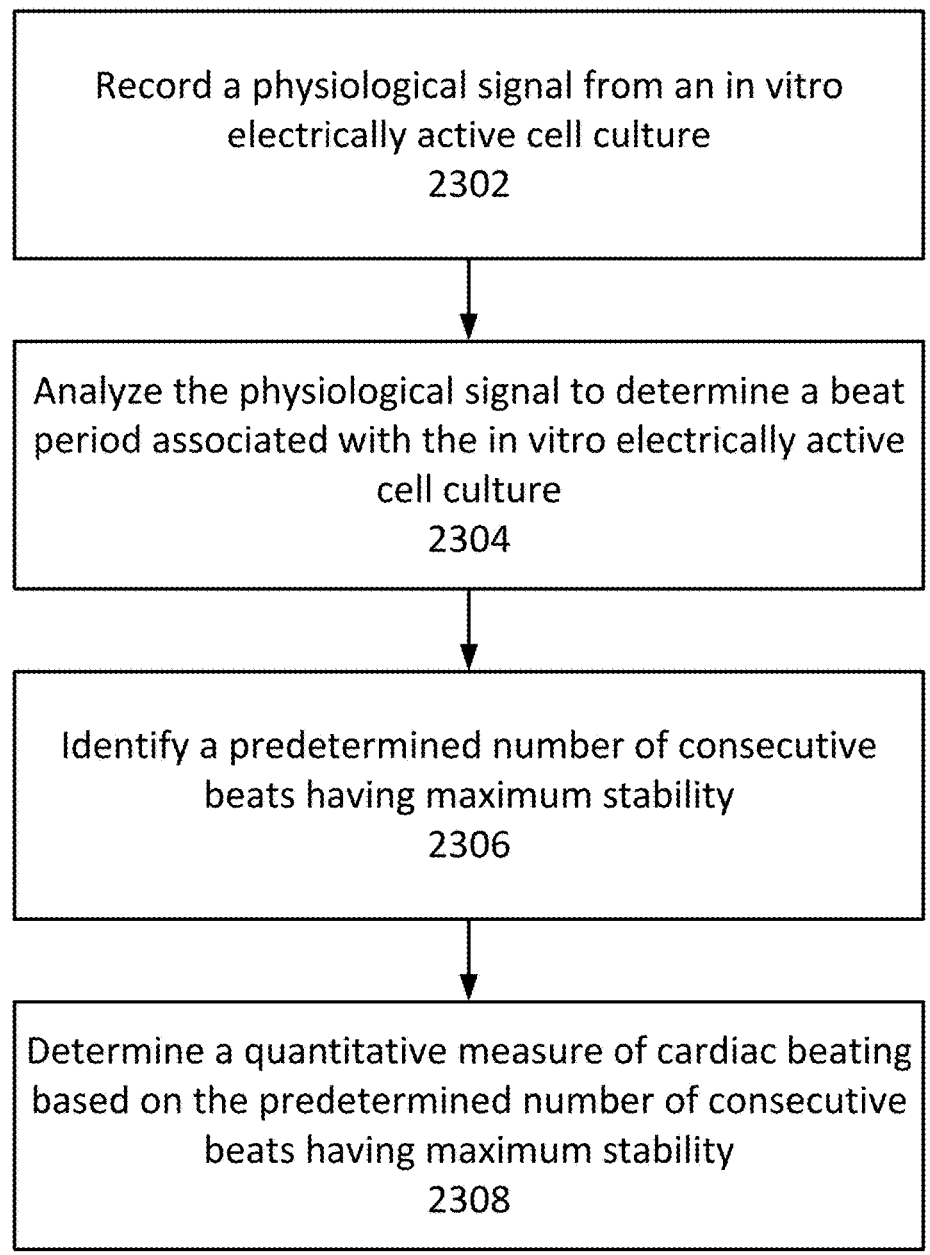
FIG. 23 is a flow diagram illustrating example operations for assessing electrically active cell culture data.

Referring now to FIG. 23, example operations for assessing electrically active cell culture data are shown. At 2302, a physiological signal from an in vitro electrically active cell culture is recorded. As described herein, the physiological signal can be recorded using a sensor such as one or more electrodes, photosensors, etc. In some implementations, the physiological signal can be recorded using an MEA, e.g., the MEA of the high-throughput electrophysiology culture system 100 of FIG. 1. The physiological signal can be transmitted to electronics (e.g., a computing device) communicatively coupled with the sensor. In addition, the physiological signal can be a cardiac beat signal. The cardiac beat signal can include at least one of a field potential signal, an impedance signal, an action potential signal, a calcium signal, an optical signal, or combinations thereof. At 2304, the physiological signal is analyzed to determine a beat period associated with the in vitro electrically active cell culture. As described herein, the beat period is the time interval from one depolarization to the next of the physiological signal, for example. At 2306, a predetermined number of consecutive beats having maximum stability is identified. The predetermined number of consecutive beats having maximum stability can be between about 5 and about 500. For example, the predetermined number of consecutive beats having maximum stability can be about 30 consecutive beats, for example. Optionally, beats having maximum stability can be identified using a coefficient of variation (or other stability metric) of beat period. Relatively lower coefficients of variation of beat period indicate that beats have relatively higher stability. On the other hand, relatively higher coefficients of variation of beat period indicate that beats have relatively lower stability. Accordingly, a predetermined number of consecutive beats having maximum stability can be identified based on the coefficients of variation. It should be understood that the coefficient of variation is provided only as an example stability metric and that other stability metrics (e.g., standard deviation) can be used to identify beats with maximum stability. At 2308, a quantitative measure of cardiac beating is determined based on the predetermined number of consecutive beats having maximum stability. In other words, the beats having maximum stability are used in the further analysis (e.g., determination of a quantitative measure) while beats having lesser stability are excluded from the further analysis. The quantitative measure of cardiac beating can include, but is not limited to, beat period, field potential duration (FPD), depolarization spike amplitude, or conduction velocity.

Figure 24:
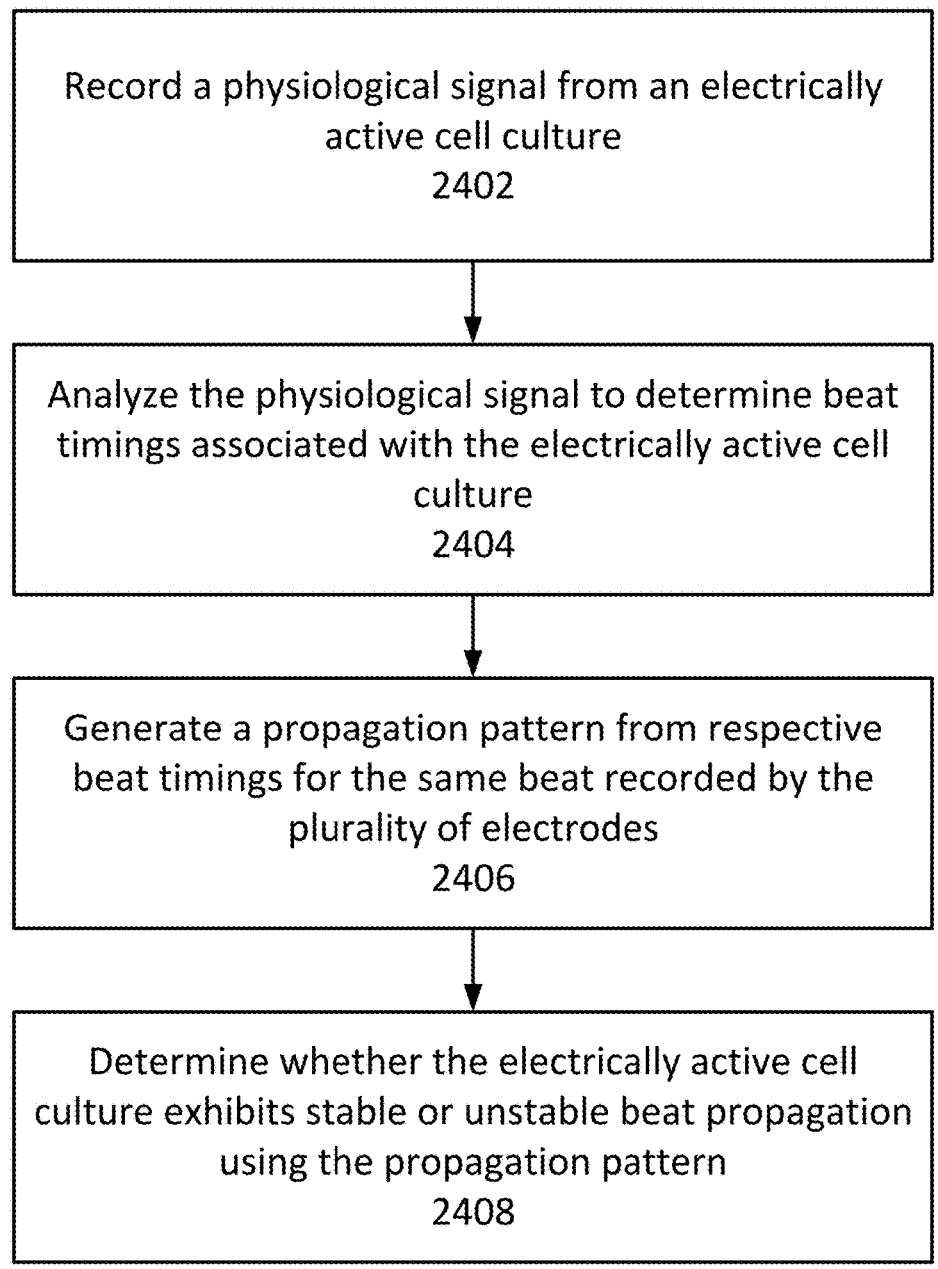
FIG. 24 is another flow diagram illustrating example operations for assessing electrically active cell culture data.

Referring now to FIG. 24, example operations for assessing electrically active cell culture data are shown. At 2402, a physiological signal from an electrically active cell culture can be recorded using a plurality of sensors. As described herein, the physiological signal can be recorded using a plurality of sensors such as an array of electrodes, photosensors, etc. In some implementations, the physiological signal can be recorded using an MEA, e.g., the MEA of the high-throughput electrophysiology culture system 100 of FIG. 1. The physiological signal can be transmitted to electronics (e.g., a computing device) communicatively coupled with the sensors. In addition, the physiological signal can be a cardiac beat signal. The cardiac beat signal can include at least one of a field potential signal, an impedance signal, an action potential signal, a calcium signal, an optical signal, or combinations thereof. At 2404, the physiological signal is analyzed to determine beat timings associated with the electrically active cell culture. At 2406, a propagation pattern is generated from respective beat timings for the same beat recorded by the plurality of sensors. Propagation patterns are described with regard to FIGS. 7A, 7B, 8A, 8B, 9B, 10A, 10B, 11, 14A, 14B, and 15. In other words, by generating a propagation pattern, beat timings can be transformed into delay maps. The propagation patterns can optionally be visually displayed, for example, using a display device of the electronics. The propagation patterns facilitate visualization of how beats start and end as they travel across the electrodes and/or MEA. The propagation patterns also facilitate visualization of beat conduction well-to-well across an MEA plate and/or beat-to-beat in the same well or in different wells of an MEA plate. At 2408, a determination is made as to whether the electrically active cell culture exhibits stable or unstable beat propagation using the propagation pattern. As described herein, beats with spatial stability follow the same propagation pattern (e.g., FIG. 9B), and irregular beats follow different propagation patterns (e.g., FIGS. 10A and 10B). Optionally, quantitative measures of beat propagation stability (including conduction velocity) can be obtained from the propagation pattern as described herein.

Throughout this application, various publications are referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. An electrophysiology culture system, comprising:
a sensor configured to record a physiological signal from an electrically active cell culture; and
an analyzer having a processor and a memory, the memory having computer-readable instructions stored thereon, wherein the processor is communicatively coupled with the sensor, the processor being configured to execute the computer-readable instructions that cause the processor to:
receive the physiological signal recorded by the sensor,
analyze the physiological signal to determine a beat period associated with the electrically active cell culture and a pro-arrhythmic indicator, wherein determining a pro-arrhythmic indicator comprises detecting a region of beat period bi-stability by estimating a probability distribution of beat period, and wherein the region of beat period bi-stability comprises a plurality of beats with a bimodal probability distribution of beat period, and
determine a quantitative measure of arrhythmia burden using a relationship between the beat period associated with the electrically active cell culture and the pro-arrhythmic indicator, wherein the relationship comprises a respective pro-arrhythmic indicator determined for each of at least two distinct beat periods.

2. The electrophysiology culture system of claim 1, wherein the probability distribution of beat period is estimated using kernel density estimation.

3. The electrophysiology culture system of claim 1, wherein the plurality of beats with the bimodal probability distribution comprise a set of beats having a short beat period and a set of beats having a long beat period.

4. The electrophysiology culture system of claim 1, wherein detecting a region of beat period bi-stability comprises classifying each of a plurality of beats as having a short beat period or a long beat period.

5. The electrophysiology culture system of claim 4, wherein the memory has further computer-readable instructions that, when executed by the processor, cause the processor to determine a quantitative measure of arrhythmia burden based on the number of beats classified as having the long beat period.

6. The electrophysiology culture system of claim 1, wherein the quantitative measure is used to assess the safety of a pharmaceutical compound in contact with the electrically active cell culture.

7. The electrophysiology culture system of claim 1, wherein the physiological signal comprises at least one of a field potential signal, an impedance signal, an action potential signal, a calcium signal, or an optical signal.

8. The electrophysiology culture system of claim 1, wherein the pro-arrhythmic indicator comprises an early after depolarization (EAD) event.

9. The electrophysiology culture system of claim 1, wherein the electrically active cell culture is an in vitro cell culture.

* * * * *